US007988674B2

(12) United States Patent
Adams et al.

(10) Patent No.: US 7,988,674 B2
(45) Date of Patent: Aug. 2, 2011

(54) EXTERNALLY RELEASABLE BODY PORTAL ANCHORS AND SYSTEMS

(75) Inventors: Matthew H. Adams, Zimmerman, MN (US); Benjamin A. Johnson, Woodbury, MN (US); James Grant Skakoon, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 1309 days.

(21) Appl. No.: 11/589,697

(22) Filed: Oct. 30, 2006

(65) Prior Publication Data

US 2008/0172068 A1     Jul. 17, 2008

(51) Int. Cl.
*A61M 5/32*     (2006.01)
*A61B 19/00*     (2006.01)

(52) U.S. Cl. ........................................ 604/174; 606/130

(58) Field of Classification Search .......... 604/174–175, 604/178; 606/129, 130
See application file for complete search history.

(56) References Cited

U.S. PATENT DOCUMENTS

| | | |
|---|---|---|
| 3,181,895 A | 5/1965 | Cator |
| 3,444,861 A | 5/1969 | Schulte |
| 3,760,811 A | 9/1973 | Andrew |
| 4,284,085 A | 8/1981 | Hansen et al. |
| 4,306,562 A | 12/1981 | Osborne |
| 4,328,813 A | 5/1982 | Ray |
| 4,350,159 A | 9/1982 | Gouda |
| 4,360,025 A | 11/1982 | Edwards |
| 5,092,850 A | 3/1992 | Buma |
| 5,231,996 A | 8/1993 | Bardy et al. |
| 5,464,446 A | 11/1995 | Dreessen et al. |
| 5,713,858 A | 2/1998 | Heruth et al. |
| 5,843,150 A | 12/1998 | Dreessen et al. |
| 5,865,842 A | 2/1999 | Knuth et al. |
| 5,916,200 A | 6/1999 | Eppley et al. |
| 5,927,277 A | 7/1999 | Baudino et al. |
| 5,954,687 A | 9/1999 | Baudino |
| 6,044,304 A | 3/2000 | Baudino |
| 6,077,250 A | 6/2000 | Snow et al. |
| 6,134,477 A | 10/2000 | Knuteson |
| 6,210,417 B1 | 4/2001 | Baudino et al. |
| 6,321,104 B1 | 11/2001 | Gielen et al. |
| 6,324,433 B1 | 11/2001 | Errico |
| 6,356,792 B1 | 3/2002 | Errico et al. |
| 6,482,182 B1 | 11/2002 | Carroll et al. |

(Continued)

FOREIGN PATENT DOCUMENTS

WO     WO 03/068304 A1     8/2003

(Continued)

OTHER PUBLICATIONS

U.S. Appl. No. 11/589,694, filed Oct. 30, 2006, Sage et al.
"KUTV: Help With a Ticking Heart Time Bomb" Oct. 25, 2005, KUTV Holdings, Inc. Retrieved from the Internet: <URL:http://kutv.com/healthyliving/local_story_298165642.html>; 3 pgs.

(Continued)

*Primary Examiner* — Theodore J Stigell
*Assistant Examiner* — Andrew M Gilbert
(74) *Attorney, Agent, or Firm* — Mueting, Raasch & Gebhardt, P.A.

(57) ABSTRACT

Embodiments of the present invention include anchor assemblies and methods for using the same to immobilize a device within a body portal. In one embodiment, the anchor assembly is utilized to immobilize a catheter relative to a covered (e.g., skin-covered) burr hole formed in a skull. Anchor assemblies in accordance with embodiments of the present invention may include anchors located subdermally that may be unlocked from outside the body to release the device without a surgical procedure.

25 Claims, 16 Drawing Sheets

U.S. PATENT DOCUMENTS

| | | | |
|---|---|---|---|
| 6,508,789 | B1 | 1/2003 | Sinnott et al. |
| 6,902,207 | B2 | 6/2005 | Lickliter |
| 2002/0052610 | A1* | 5/2002 | Skakoon et al. .............. 606/129 |
| 2003/0199831 | A1 | 10/2003 | Morris et al. |
| 2005/0054985 | A1 | 3/2005 | Mogg |
| 2005/0107739 | A1 | 5/2005 | Palma |
| 2005/0119719 | A1 | 6/2005 | Wallace et al. |
| 2005/0182420 | A1 | 8/2005 | Schulte et al. |
| 2005/0182421 | A1 | 8/2005 | Schulte et al. |
| 2005/0182422 | A1 | 8/2005 | Schulte et al. |
| 2005/0182423 | A1 | 8/2005 | Schulte et al. |
| 2005/0182424 | A1 | 8/2005 | Schulte et al. |
| 2005/0182425 | A1 | 8/2005 | Schulte et al. |
| 2005/0182464 | A1 | 8/2005 | Schulte et al. |
| 2006/0129126 | A1 | 6/2006 | Kaplitt et al. |
| 2006/0135945 | A1 | 6/2006 | Bankiewicz et al. |

FOREIGN PATENT DOCUMENTS

| | | |
|---|---|---|
| WO | WO 2004/026161 A2 | 4/2004 |
| WO | WO 2004/026161 A3 | 7/2004 |
| WO | WO 2004/026161 A3 | 8/2004 |

OTHER PUBLICATIONS

Roberts, "New surgery open-and-shut case" Kansas City Business Journal, May 5, 2006; 1pg.

"STIMLOC by ign," datasheet, Image Guided Neurologics, Inc. © 2004 Image Guided Neurologics, Inc., Melbourne, FL, Retrieved from the Internet: <URL: http://www.igneurologics.com/pages/dba2/stimloc.pdf>; 2 pgs.

Sanftner et al., "AAV2-mediated gene delivery to monkey putamen: evaluation of an infusion device and delivery parameters" *Experimental Neurology*, 2005; 194:476-483.

* cited by examiner

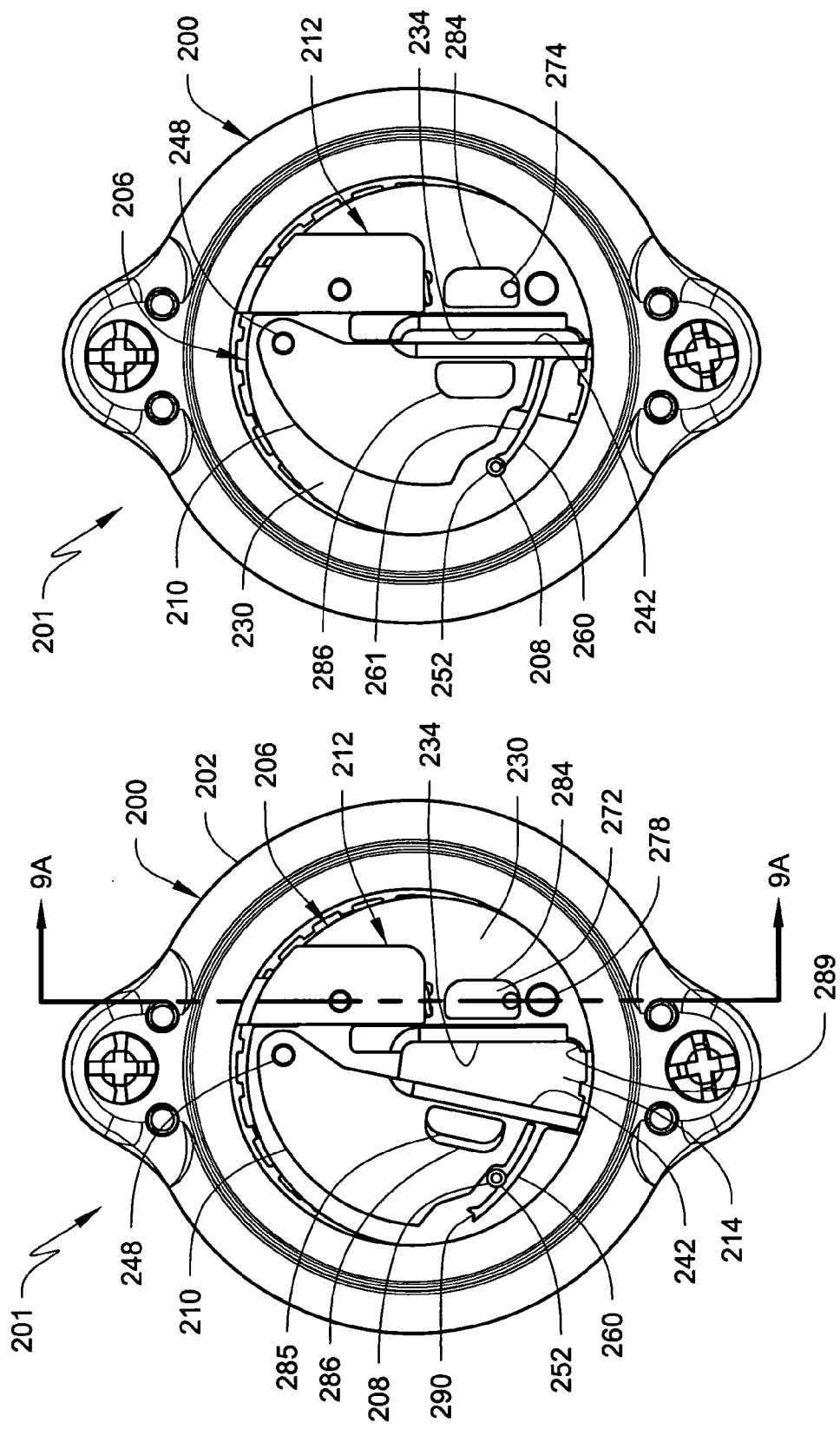

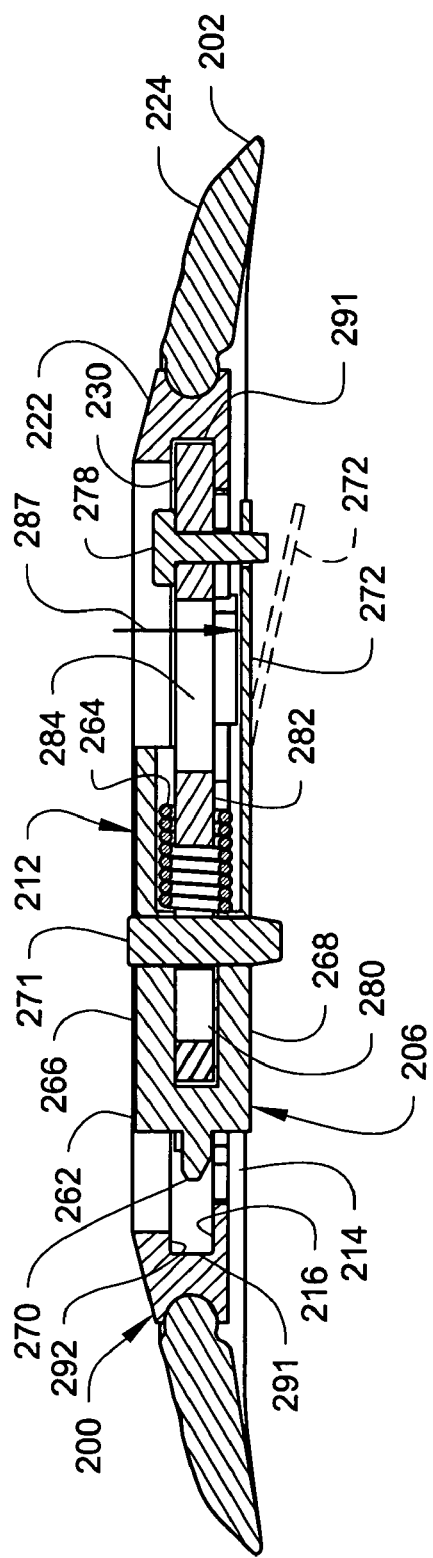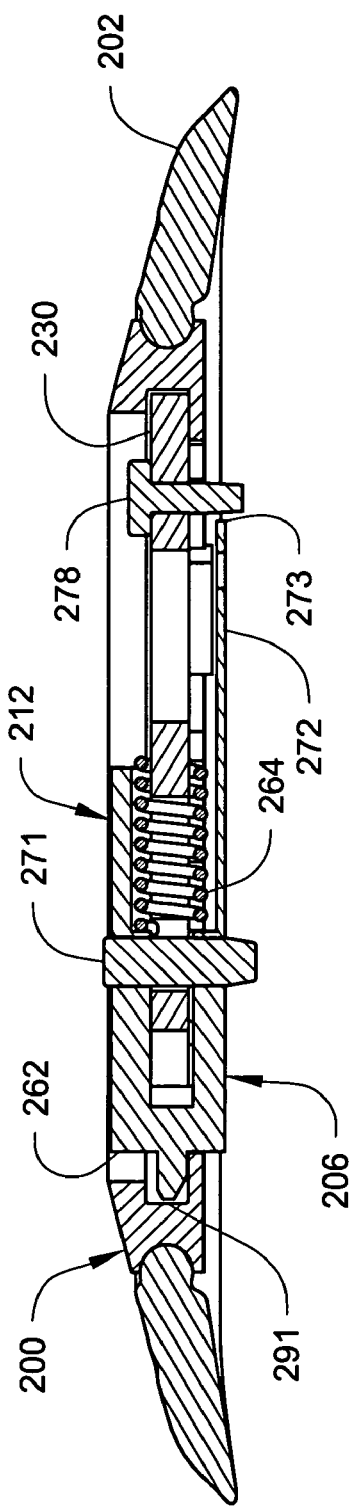

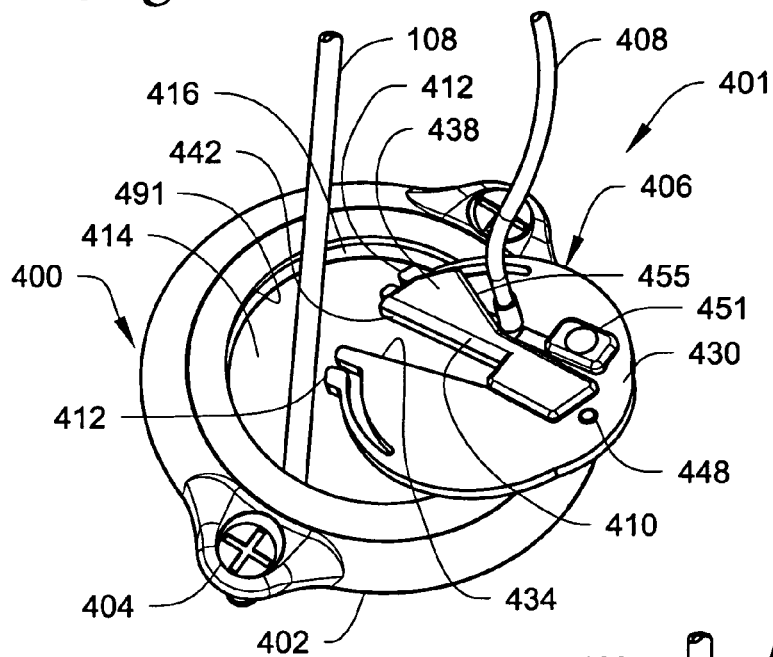
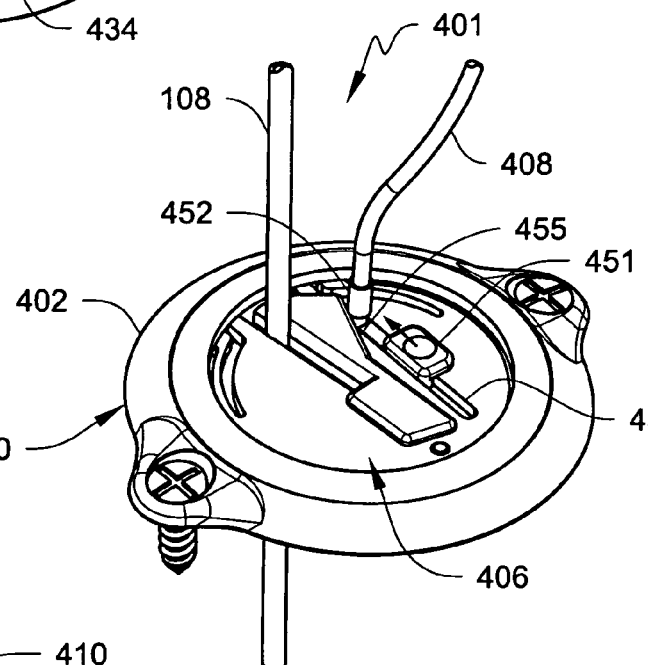
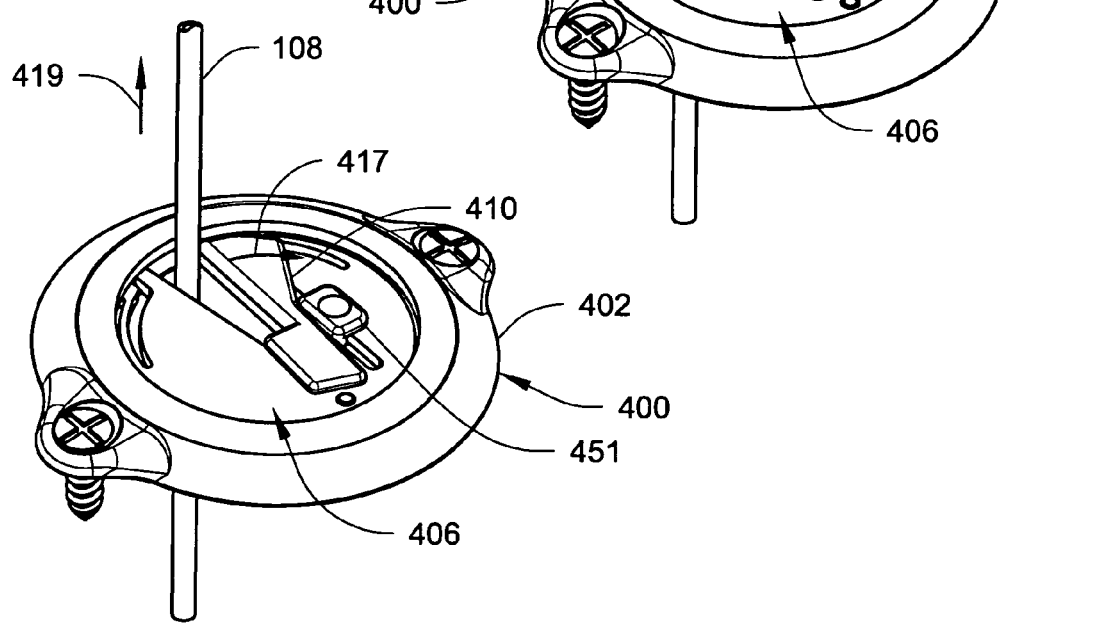

EXTERNALLY RELEASABLE BODY PORTAL ANCHORS AND SYSTEMS

TECHNICAL FIELD

The present invention relates generally to medical devices and, more particularly, to releasable, subdermal anchors for securing a therapy delivery device (e.g., a catheter or electrical stimulation lead) within a body portal such as a burr hole, and to systems and methods incorporating the same.

BACKGROUND

Medical procedures involving access to the brain through a burr hole in the skull are used to treat a variety of medical conditions. For example, electrical stimulation of the brain to relieve chronic pain, or for the treatment of movement disorders, may necessitate access via a burr hole. Similarly, burr holes are typically formed to allow implantation of a catheter, e.g., a parenchymal or intracerebroventricular catheter, to treat various ailments.

Use of a catheter to deliver a therapeutic agent to the brain generally involves the insertion of the catheter into the brain and dispensing the agent at the desired location. During a typical implantation procedure, an incision may be made in the scalp to expose the patient's skull. After forming a burr hole through the skull, the catheter may be inserted into the brain. To accurately place the catheter and avoid unintended injury to the brain, surgeons typically use stereotactic apparatus/procedures. One exemplary stereotactic apparatus is described in U.S. Pat. No. 4,350,159 to Gouda, which may be used to position, for example, an electrode.

As one can appreciate, once an inserted device such as a catheter is properly positioned, it is important that it be adequately immobilized to prevent movement from its intended location. Even minimal movement of the device tip may yield unsatisfactory therapeutic results. Accordingly, reliable methods and apparatus for anchoring and securing the device relative to the burr hole are needed.

Exemplary burr hole anchor devices include those described in U.S. Pat. No. 4,328,813 to Ray and U.S. Pat. No. 5,927,277 to Baudino et al. Ray discloses, among other features, a socket and plug arrangement in which the plug is positioned so as to trap a positioned electrical stimulation lead between the socket and plug. Baudino et al. discloses, among other features; an apparatus and method that allows anchoring of a device to occur before it is detached from the stereotactic apparatus, thereby reducing the potential for inadvertent movement during subsequent implantation steps.

While effective for their intended purposes, many known anchor devices are, for the most part, used primarily to secure the implanted catheter or lead for long term implantation. Some therapies (e.g., acute gene therapy for the treatment of Parkinson's disease), however, are delivered for a more limited period of time, e.g., a few hours to a few days or less. Accordingly, in the case of the latter, it may be beneficial to completely remove the catheter at therapy completion. Yet, device (e.g., catheter) removal generally requires a surgical procedure to: expose the burr hole and anchor; release the catheter from the anchor; remove the catheter; and close the incision. Such a removal procedure may, however, be undesirable for various reasons, including cost and potential patient apprehension associated with another surgical procedure.

SUMMARY

The present invention may overcome these and other issues with known anchors and anchor systems by providing, among other features, devices and systems that permit external manipulation of the anchor to release the device. As a result, the anchor may be configured to selectively release the device (e.g., catheter) without the need for a secondary surgical procedure.

In one embodiment, an anchor assembly for securing a device relative to a skin-covered portal is provided. The anchor assembly includes a retainer positionable in or near the portal and beneath the skin. The retainer includes: a body portion including a peripheral edge and a first retaining surface; and an arm attached to the body portion. The arm includes a second retaining surface movable, relative to the first retaining surface, between a first position and a second position. The anchor assembly further includes a lock member attachable to the body portion and movable from an engaged state in which the lock member holds the arm in the second position, to a disengaged state in which the lock member releases the arm from the second position. The lock member is movable from the engaged state to the disengaged state via manipulation of the lock member from outside the skin.

In another embodiment, an anchor assembly for securing a therapy delivery device relative to a burr hole is provided. The anchor assembly includes an anchor having a base with a peripheral portion defining a central opening; and a retainer attachable to the base in or near the central opening. The retainer includes a body portion defining a mounting plane, wherein the body portion includes a peripheral edge and a first retaining surface formed by an edge of an opening extending through the peripheral edge. The retainer further includes an arm movably attached to the body portion, the arm having a second retaining surface movable, relative to the first retaining surface, between a first position and a second position. The anchor assembly further includes a lock member removably coupled to the body portion and protruding outwardly in a direction generally orthogonally from the mounting plane of the body portion.

In yet another embodiment, a system for delivering a therapeutic agent to brain tissue via a burr hole formed in a skull is provided. The system includes a brain catheter having an indwelling portion positionable through the burr hole, and an external portion routable through skin covering the skull. An anchor assembly attachable to the skull in or near the burr hole is also provided. The anchor assembly is operable to immobilize the brain catheter relative to the burr hole. The anchor assembly includes a lock member to selectively release the brain catheter from the anchor assembly, the lock member releasable from a location outside of the skin.

In yet another embodiment, a method for delivering therapy via a partially implanted device extending through a skin-covered burr hole is provided. The method includes securing the device relative to the burr hole with an anchor assembly, wherein the anchor assembly includes a subdermal anchor fixed relative to bone surrounding the burr hole. The device may protrude outwardly through an opening in the skin. The method further includes releasing the device from the anchor by manipulation of the anchor assembly from outside the skin; and applying a force to a portion of the device that protrudes outside the skin to remove the device.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTION OF THE VIEWS OF THE DRAWING

The present invention will be further described with reference to the figures of the drawing, wherein:

FIGS. 1A-1B illustrate an infusion system incorporating an anchor assembly having an anchor (e.g., a burr hole anchor) in accordance with one embodiment of the invention, wherein: FIG. 1A is a diagrammatic view of the system implanted in a human body; and FIG. 1B is a view of the system removed from the body;

FIG. 7 is a top plan view of the anchor assembly of FIG. 5 with the arm shown in the unlocked position, but with the latch shown in the latched position;

FIG. 8 is a top plan view of the anchor assembly of FIG. 6 with the arm shown in the locked position and the latch shown in the latched position;

FIGS. 9A-9B illustrate section views of the anchor assembly of FIG. 7, wherein: FIG. 9A is a section view taken along line 9A-9A of FIG. 7 but with the latch of the retainer shown in the unlatched position; and FIG. 9B is a section view similar to that of FIG. 9A, but with the latch of the retainer shown in the latched position;

FIGS. 11A-11D illustrate an exemplary method for using the anchor assembly of FIGS. 1A-1B, wherein: FIG. 11A illustrates attachment of the anchor base to the skull; FIG. 11B illustrates insertion of the anchor retainer into the anchor base; FIG. 11C illustrates external portions of the anchor assembly and catheter after an implantation incision is closed; and FIG. 11D illustrates unlocking and removal of the catheter at therapy completion;

FIGS. 12A-12B illustrate an anchor assembly in accordance with an alternative embodiment of the invention, wherein: FIG. 12A is a perspective view of the anchor assembly during assembly of an anchor retainer with an anchor base; and FIG. 12B illustrates the anchor assembly after assembly and with the retainer shown in a first or unlocked configuration corresponding to an arm of the retainer being in a first or unlocked position;

FIGS. 14A-14B illustrate an optional cap for use with the anchor assembly of FIGS. 12A-12B, wherein: FIG. 14A is a bottom perspective view prior to attachment of the cap; and FIG. 14B is a top perspective view after attachment of the cap; and FIGS. 15A-15D illustrate an anchor assembly in accordance with yet another embodiment of the invention, wherein: FIG. 15A is a perspective view of the anchor assembly during attachment of an anchor retainer with an anchor base; FIG. 15B illustrates immobilization of the catheter; FIG. 15C illustrates release of the catheter, e.g., at therapy completion; and FIG. 15D illustrates a bottom perspective view of the anchor assembly of FIGS. 15A-15C.

Figure 1A:
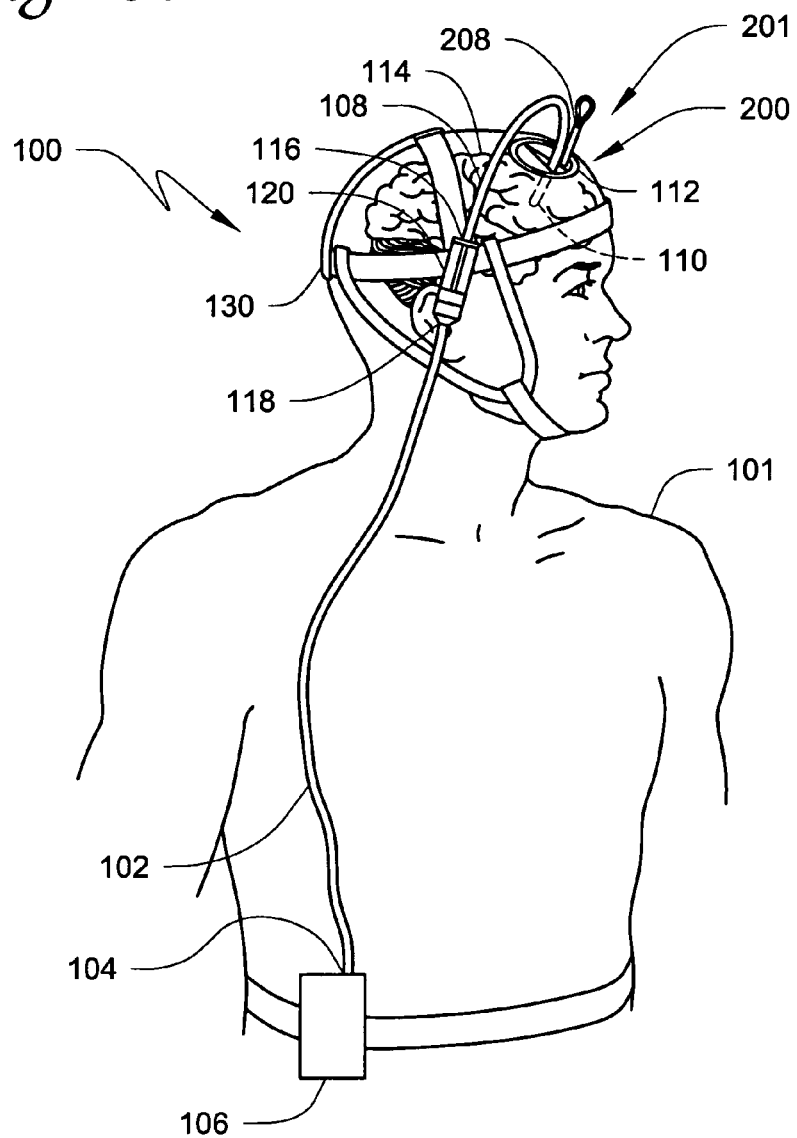

The figures are rendered primarily for clarity and, as a result, are not necessarily drawn to scale.

DETAILED DESCRIPTION OF EXEMPLARY EMBODIMENTS

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the invention.

Embodiments of the instant invention are directed to anchor devices and assemblies and to corresponding systems and methods for securing a therapy delivery device relative to a surface, e.g., a surface of a body. For example, exemplary anchor assemblies and devices described herein may be configured to secure a therapy delivery device (such as a stimulation lead or infusion catheter) that is partially implanted through a skin-covered body portal. Moreover, these anchor assemblies may be manipulated from a location outside of the skin (e.g., outside of the patient's body) to release the therapy delivery device, e.g., at therapy completion. Once released, the device may be withdrawn from the body, e.g., by application of an external force or other action. As a result, the device may be removed from the patient without a separate surgical procedure.

While the term "skin" is used herein to identify an exemplary covering of the body portal, this term is not to be read in a limiting sense. That is, embodiments of the present invention are equally applicable to portals covered by most any material, including grafts, medical dressings, and other synthetic and biologic coverings, as well as to uncovered portals.

In the described embodiments, an anchor portion of the anchor assembly is configured as a burr hole anchor. The anchor may be part of a system for infusing a therapeutic agent into the patient's brain via a brain catheter passing through a burr hole formed in the skull. The anchor, which may be subdermally located, may be used to secure the catheter relative to the burr hole. The anchor assembly may include the anchor as well as a lock member to release the catheter from the anchor at therapy completion.

While described herein in the context of burr hole anchors and corresponding infusion systems, anchor assemblies and systems in accordance with embodiments of the present invention may find use in most any medical (or non-medical) application that involves access through a portal formed in a surface.

It is noted that the terms "comprises" and variations thereof do not have a limiting meaning where these terms appear in the accompanying description and claims. Moreover, "a," "an," "the," "at least one," and "one or more" are used interchangeably herein.

Relative terms such as left, right, forward, rearward, top, bottom, side, upper, lower, horizontal, vertical, and the like may be used herein and, if so, are from the perspective observed in the particular figure. These terms are used only to simplify the description, however, and not to limit the scope of the invention in any way.

Figure 1B:
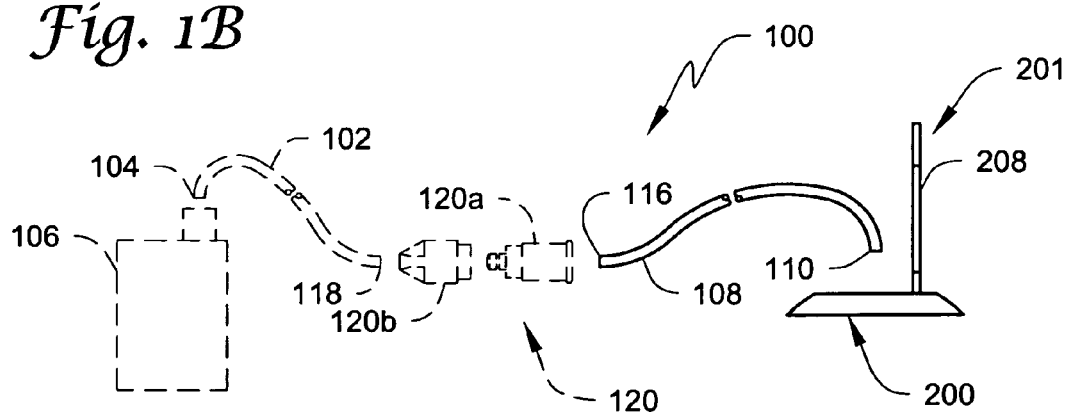

FIGS. 1A and 1B illustrate an exemplary implantable medical system, such as a brain infusion catheter system 100. FIG. 1A illustrates the system as it may be configured during use, e.g., implantation, while FIG. 1B illustrates the system removed from the body.

The exemplary infusion system 100 may include a first medical tube, e.g., brain catheter 108, partially implanted within the body 101. A second medical tube 102 may also be provided having a distal end 104 coupled to an external reservoir (e.g., infusion pump 106) containing a volume of the therapeutic agent (as used herein, the terms "distal" and "proximal" are taken from the reference of a connector 120 as shown in FIG. 1A). The infusion pump 106 may be identical or similar in construction to insulin pumps such as the Paradigm 515 or 715 pumps produced by Medtronic MiniMed of Northridge, Calif., USA. In the illustrated example, the brain catheter 108 has an indwelling portion, e.g., a distal end 110, implanted through a body portal (e.g., burr hole 112) and located at a predetermined location within the brain 114 of the patient. An external portion (e.g., a proximal end 116) of the brain catheter 108 may be routable through skin covering the skull 113 (see FIG. 2) and extend outside the body 101 where it connects to a corresponding proximal end 118 of the tube 102, e.g., via the connector 120.

While described herein in the context of a pump 106, this configuration is not limiting. For example, other embodiments may replace the pump with most any medicament delivery device, e.g., syringe, drip bag, etc., without departing from the scope of the invention.

The breakaway connector 120 may include a first connector portion 120a coupled to the brain catheter 108 and a second connector portion 120b coupled to the tube 102 as shown in FIG. 1B. The first connector portion 120a is operable to separate from the second connector portion 120b when a traction force applied between the tube 102 and the brain catheter 108 reaches a predetermined threshold value. That is, the connector 120 may be configured to separate once a predetermined traction force is applied across the connector, e.g., between the tubes 102 and 108. The connector 120 may utilize either frictional or non-frictional (e.g., magnetic) interfaces to achieve the breakaway function. The breakaway function may be beneficial to reduce inadvertent catheter dislodgement as the result of snagging of the tube 102 or other system 100 components on surrounding objects.

In the illustrated embodiment, the connector 120 may be supported, e.g., pivotally supported, by an optional headgear apparatus 130 (see FIG. 1A) formed from a series of adjustable, fabric (e.g., nylon webbing) or elastic bands. The headgear apparatus 130 may hold the connector, e.g., via a connection with the first connector portion 120a, during the implantation. While illustrated as supported by the headgear apparatus 130 in FIG. 1A, the connector 120 could alternatively be generally unsupported, e.g., supported only by the free proximal ends 116 and 118 of the catheter 108 and tube 102, respectively, without departing from the scope of the invention. An exemplary breakaway connector 120 is described and illustrated in a related U.S. Patent Application entitled BREAKAWAY CONNECTORS AND SYSTEMS (U.S. patent application Ser. No. 11/589,694, filed on even date herewith and incorporated by reference herein in its entirety). The use of other connector configurations that may provide a breakaway function are certainly possible. For example, connectors using a snap-fit lock (e.g., similar to that disclosed by Lickliter in U.S. Pat. No. 6,902,207) or those incorporating a magnetic lock (e.g., similar to that disclosed by Cator in U.S. Pat. No. 3,181,895) could be used.

The system may further include a portal anchor device, e.g., burr hole anchor 200. The anchor 200 may attach to the body, e.g., to the skull 113, in or near the burr hole 112. The anchor 200 may be used to selectively immobilize the catheter 108 relative to the burr hole 112. In the illustrated embodiment, all, or substantially all, of the anchor 200 is positioned subdermally (e.g., below the skin). The anchor 200 forms part of an anchor assembly 201 that further includes a lock member 208 capable of selectively releasing the brain catheter 108 from the anchor. The lock member (further described below) may be releasable, or otherwise actuatable, from a location outside of the skin.

The system 100 may, in one embodiment, be configured to deliver a therapeutic agent containing a virally mediated gene therapy as an acute treatment for Parkinson's disease. The therapeutic agent is delivered, via the first and second tubes 108 and 102, from the pump 106 to the brain 114. This application is not limiting, however, as the system may be configured to deliver most any therapeutic agent (e.g., chemotherapy) to most any area of the body without departing from the scope of the invention. Moreover, while the embodiments described and illustrated herein are directed to catheter implantation, this is not limiting as most any other therapy delivery device (e.g., stimulation lead) may be used without departing from the scope of the invention.

Figure 2:
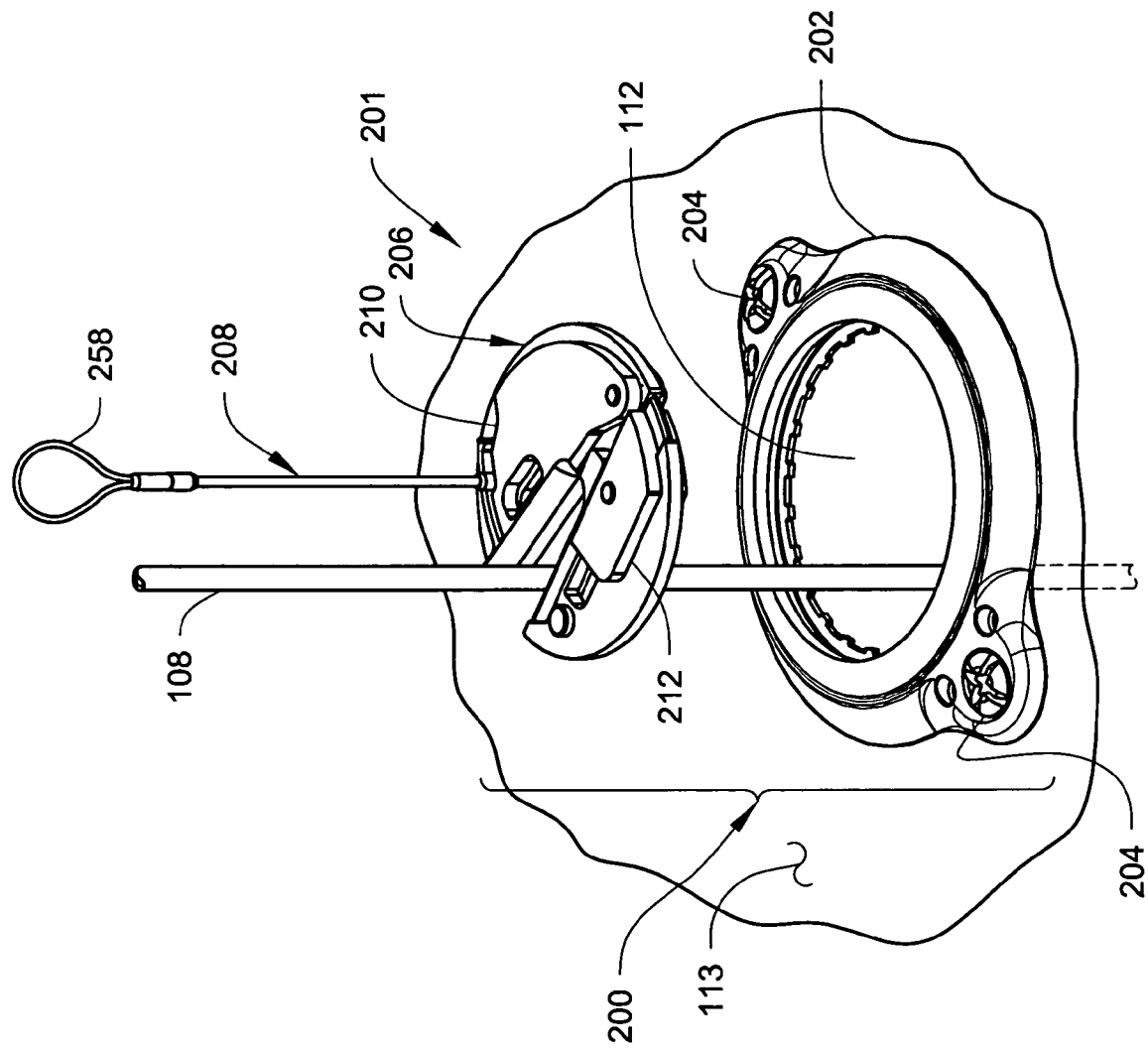
FIG. 2 is a perspective view of the anchor assembly of FIGS. 1A-1B with a base of the anchor shown attached to the body, e.g., skull, and a retainer of the anchor shown before attachment to the base.

FIG. 2 is a perspective view of the portal, e.g., burr hole, site and illustrates an anchor system in accordance with one embodiment of the invention. The burr hole 112 may be formed through the skull 113 in a known manner prior to catheter 108 implantation. In the illustrative embodiment, the anchor 200 includes a base 202 that at least partially surrounds the portal (burr hole 112) and is attachable to tissue surrounding the portal, e.g., to the skull 113, with fasteners, e.g., bone screws 204, or the like. The anchor 200 may further include a retainer 206 (shown exploded from the base in FIG. 2) that is attachable or otherwise securable to the base 202 and is capable of selectively gripping or otherwise immobilizing the catheter 108. In some embodiments, the base 202 may be optional. That is, the retainer 206 could be positionable in or near the burr hole portal beneath the skin, where it may be secured to the skull in another manner, e.g., friction. The retainer 206 may include a movable arm 210 and a latch or latching device 212, each of which is described in more detail below. The components of the retainer 206 (e.g., body portion 230 and arm 210) may be constructed of most any biocompatible material, but are, in one embodiment, made from titanium.

Figure 3:
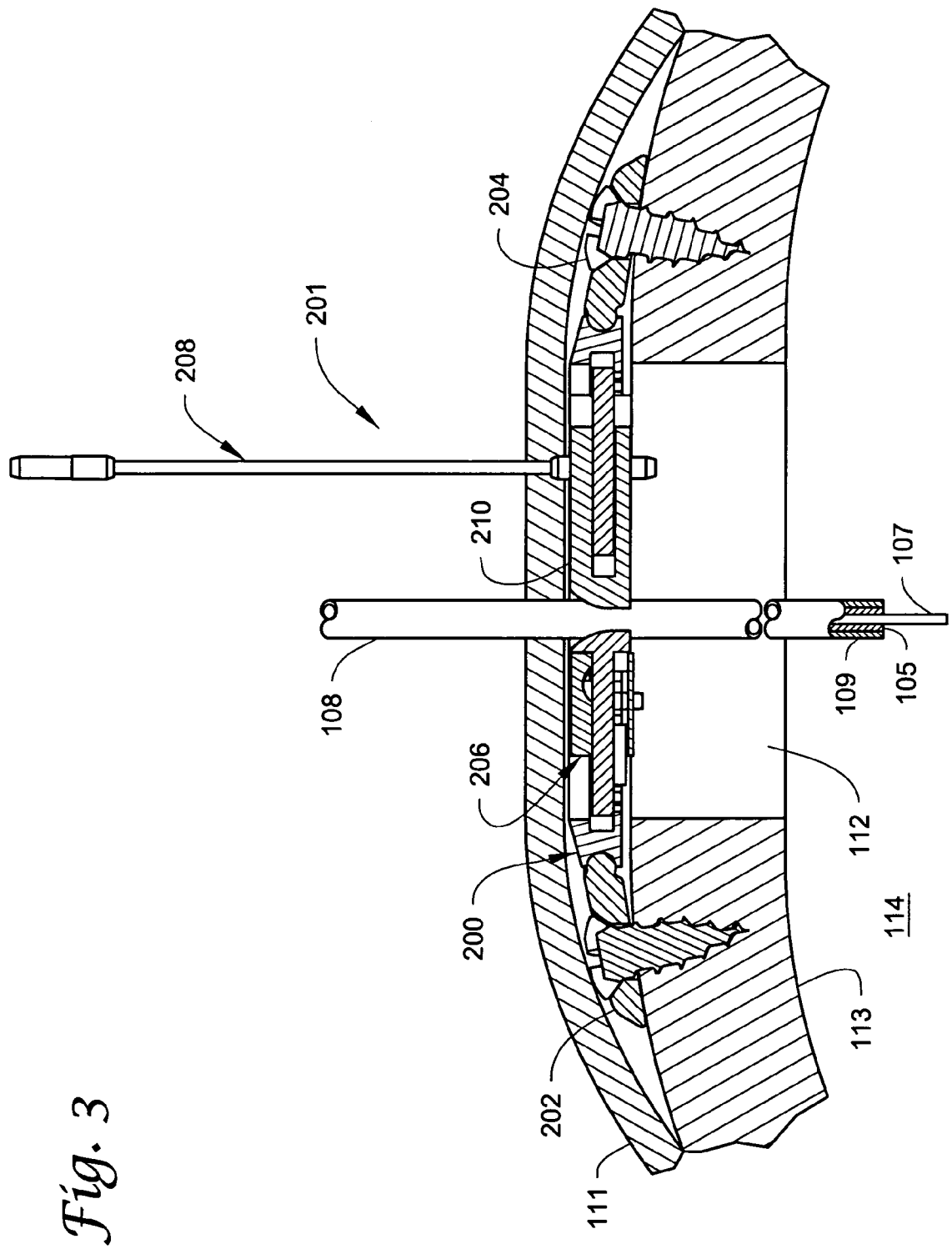
FIG. 3 is a cross section of the anchor assembly of FIGS. 1A-1B as it may be implanted within the body.

FIG. 3 illustrates a cross sectional view of the anchor assembly 201 and catheter 108 after implantation. As evident in this view, the anchor 200, e.g., the base 202 and retainer 206, are operable to be subdermally located (i.e., beneath the skin 111). As FIG. 3 further illustrates, the arm 210 may move from a first or unlocked position shown in FIG. 2 (corresponding to the retainer being in a first or unlocked configuration), to a second or locked position shown in FIG. 3 (corresponding to the retainer being in a second or locked configuration). In the second position, opposing retaining surfaces 234 and 242 (see FIG. 4) may mechanically engage the catheter 108 and hold it in place relative to the burr hole 112. The lock member 208 may be configured to hold or secure the arm 210 in the second position. The catheter 108 and the lock member 208 may, at the completion of implantation surgery, extend outwardly through the skin 111 covering the skull 113 and the now-implanted anchor 200.

Figure 4:
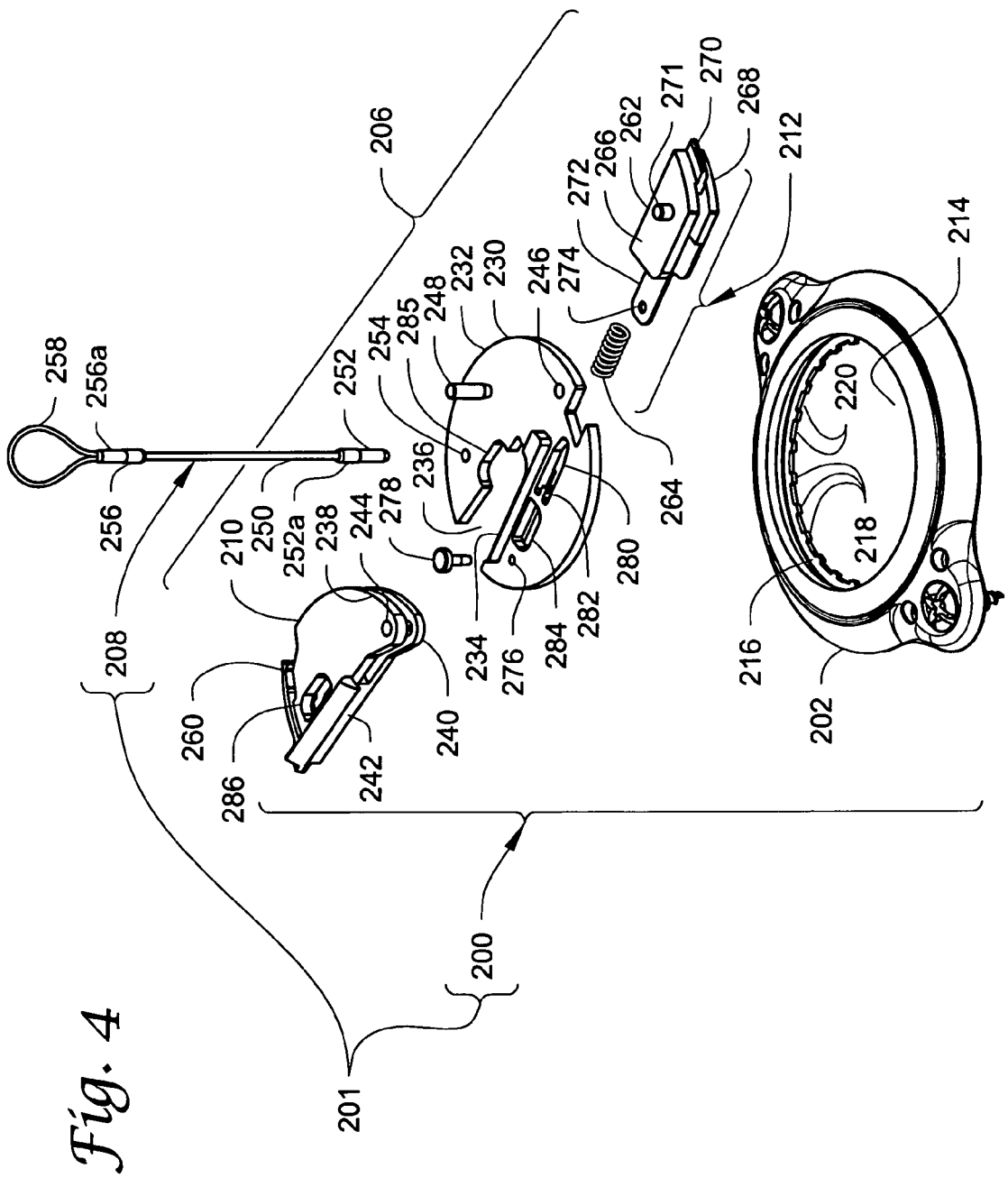
FIG. 4 is an exploded perspective view of the anchor assembly of FIGS. 1A-1B.

FIG. 4 is a perspective view of the base 202 with the retainer 206 exploded to illustrate an exemplary construction. In this embodiment, the retainer 206 includes a planar, disk-shaped body or body portion 230 that defines a mounting plane. The base 202 may form a peripheral portion of the anchor 200 that defines a central opening 214. An inner surface of this peripheral portion may form a ledge 216 to receive and support a peripheral edge 232 of the body portion 230 when the retainer is attached to the base in or near the central opening.

The ledge 216 may, in one embodiment, be formed by a plurality of teeth 218 protruding from the inner surface of the peripheral portion into the central opening 214. A recess 220 may be defined between adjacent pairs of the plurality of teeth 218.

The body portion 230 may further include a first retaining surface 234 defined by an edge of a cutout or pie-shaped opening 236 extending through the peripheral edge 232. The first retaining surface 234 may span from an interior of the body portion 230 to a location at or near the peripheral edge 232. As further explained below, the first retaining surface 234 may be configured to mechanically engage the catheter 108 (not shown in FIG. 4) during use.

The arm 210 may be movably, e.g., pivotally, attached to the body portion 230. For example, the arm 210 may include a second retaining surface 242 that joins first and second plate members 238, 240. The plate members 238, 240 may form a clevis extending over both sides of the body portion 230 when the arm 210 is assembled with the body portion.

Figure 5:
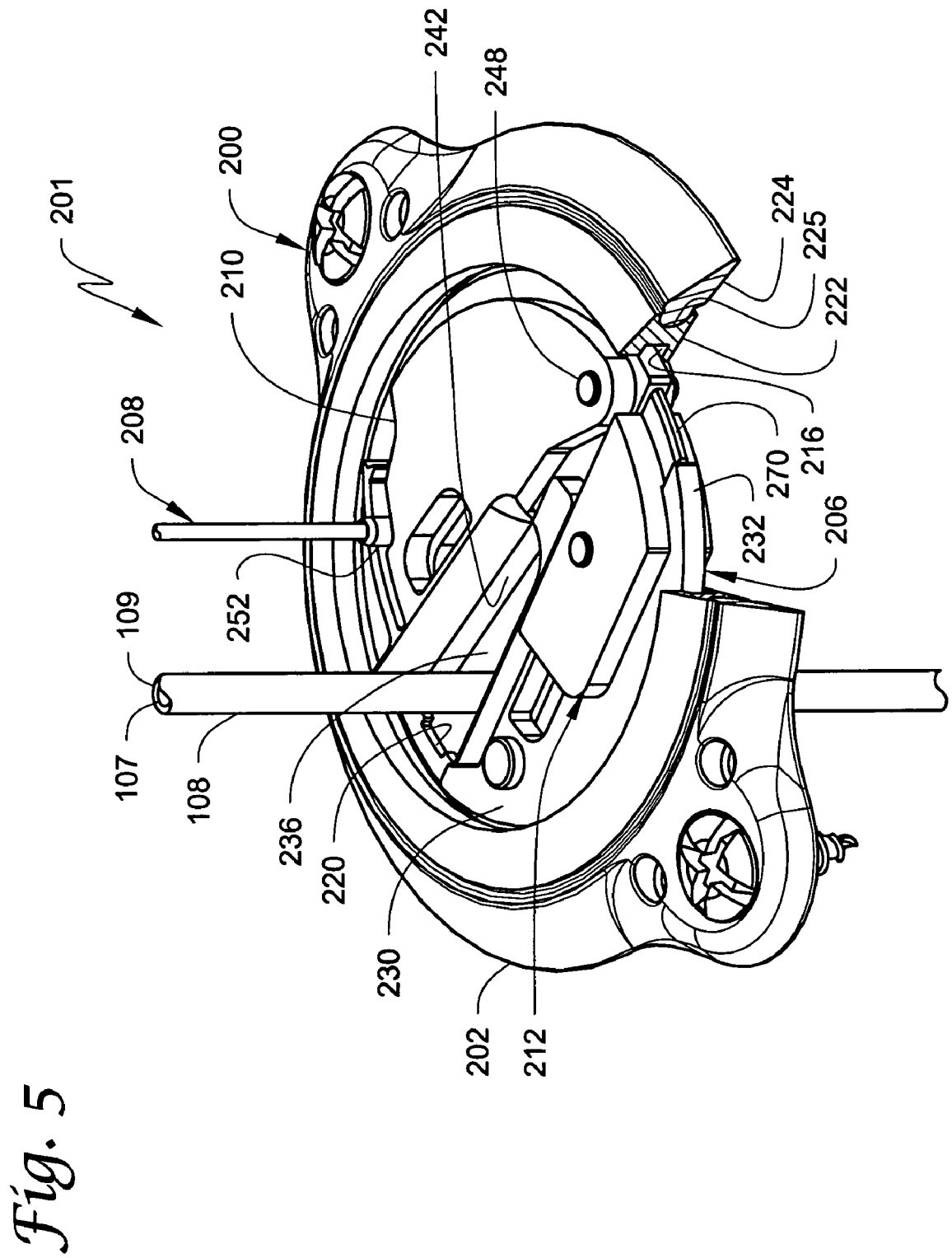
FIG. 5 is a partial cut-away view of the anchor of FIGS. 1A-1B, wherein the retainer is shown in a first or unlocked configuration corresponding to an arm of the retainer being in a first or unlocked position, and further wherein a latch of the retainer is shown in a first or unlatched position.

The two plate members 238, 240 may include openings 244 that align with an opening 246 in the body portion 230 such that a pin 248 may be inserted through the openings (the pin 248 may engage either the arm 210 or the body portion 230 with interference) as shown in FIG. 5. The arm 210 may thus pivot about an axis of the pin 248. The second retaining surface 242, e.g., the arm 210, is therefore movable, relative to the first retaining surface, between the first position configured to receive the catheter 108 (see, e.g., FIG. 5), and the second position configured to mechanically engage the catheter (e.g., via friction or via a biting or clamping action) against the first retaining surface 234 (see, e.g., FIG. 6). Thus, the catheter 108 may be immobilized or otherwise locked relative to the anchor 200 via a pivoting motion applied to the arm 210.

In embodiments wherein the catheter 108 is engaged via a biting action or a high frictional force, the catheter may be constructed of a compliant material that can withstand the contact forces of the first and second retaining surfaces without occluding the catheter, e.g., an elastomeric material (pure or blended) such as a polymer, silicone, or the like.

In one particular embodiment, the catheter 108 may include a tubular core 107 (see, e.g., FIGS. 3 and 5) made from flexible tubing that is resistant to compression and collapse, e.g., silica or quartz capillary tubing, PEEK capillary tubing, or stainless steel capillary tubing. The tubular core 107 may have an inner diameter of about 100 micrometers and an outer diameter of about 200 micrometers, e.g., about 193 micrometers. An exemplary core 107 may be a flexible synthetic fused silica capillary having an optional protective polymer (e.g., polyimide) coating such as the TSP line of products sold by Polymicro Technologies, LLC, of Phoenix, Ariz., USA.

A flexible outer covering 109 such as a polyurethane jacket having an outer diameter of about 1 millimeter, and a hardness of about 55 Shore D (at the completion of manufacture) may be formed over the tubular core 107. The flexible outer covering 109 may permit high mechanical clamping/indentation forces to be applied to the catheter, while the tubular core 107 prevents catheter occlusion under such high forces. In some embodiments, the tubular core 107 may protrude longitudinally beyond the flexible outer covering 109 at one or both ends of the catheter, e.g., about 10 mm. In still yet other embodiments, strengthening members 105, e.g., helically-wound braided members and/or straight longitudinal members, may be sandwiched between the core 107 and the flexible outer covering 109 or embedded within the outer covering. Exemplary strengthening members may include steel, polyester (e.g., polyethylene terepthalate (PET)), synthetic polymers such as Kevlar brand fiber (sold by E.I. du Pont de Nemours of Wilmington, Del., USA), and liquid crystal polymers.

The outer covering 109 may be applied to the tubular core in any known fashion. For example, it may be applied over the core 107 through a secondary extrusion process. Alternatively, the outer covering 109 may form a tube which slides over the tubular core 107 with clearance. A shrink-wrap tube may then be placed over the assembled tubes and the entire assembly heated. Any optional strengthening members, e.g., woven fibers, may also be placed over the tubular core 107 or the outer covering 109 before the heat shrink tube is applied. Subsequent heating of the assembly may cause the outer covering 109 to melt and the shrink-wrap tube to constrict. Thus, the shrink-wrap tube may force the melted outer covering (and optional strengthening members) inwardly towards the tubular core 107 and bond to the same. The shrink-wrap tube may then be removed to produce the catheter 108.

The tube 102, may, on the other hand, be constructed from conventional medical tubing such as polyurethane, silicone, or co-extrusions such as silicone/nylon or silicone/polyurethane. Alternatively, the tube 102 could be made from plasticized polyvinyl chloride (e.g., flexible PVC). In one embodiment, the tube 102 may have an inner diameter of about 0.07 mm to about 0.08 mm (e.g., about 0.076 mm) and an outer diameter of about 1.4 mm to about 1.5 mm (e.g., about 1.47 mm). While exemplary embodiments of the catheter and tube are so described above, variations in material, construction, and size of the catheter 108 and tube 102 are certainly possible without departing from the scope of the invention.

When the arm 210 is in the first position, the second retaining surface 242 may be oblique to the first retaining surface 234, e.g., a line contained within the second retaining surface may intersect a line contained within the first retaining surface at an acute angle. This configuration provides for a larger opening in which to initially insert and position the catheter as shown in FIG. 5. However, when the arm is in the second locked position (see, e.g., FIG. 6), the first and second retaining surfaces are generally parallel to one another to permit generally equivalent contact force on the catheter regardless of the catheter's position along the retaining surfaces.

In addition to the anchor 200, the anchor assembly 201 may further include the lock member 208. The lock member 208 may be formed by an elongate member or cord 250 that is removably coupled to the anchor, e.g., to the body portion 230 of the retainer 206. In one embodiment, the lock member 208, e.g., the cord 250, protrudes away from the body 230 portion generally orthogonally from the mounting plane defined by the body portion. The cord 250, in the illustrated embodiment, is configured to protrude through an opening or incision in the skin 111 as shown in FIG. 3. In one embodiment, the elongate cord 250 is made from stainless steel stranded cable, e.g., 1×7, 1/64 inch diameter.

The exemplary lock member 208 may also include a first end 252 and a second end 256. The first end 252 may be attachable to the body portion 230, e.g., detachably inserted into or otherwise received within an opening 254 formed in the body portion (see, e.g., FIG. 3). The opening 254 may position the lock member 208, e.g., the first end 252, such that it may interact with the arm 210 as further described below. In the illustrated embodiment, the lock member 208 is securely retained in the body portion 230 during the implantation period and up until the lock member 208 is intentionally removed. Such secure retention may be achieved in any number or ways, some of which are described in more detail below.

The first and second ends 252 and 256 of the lock member 208 may be formed by sleeves 252a and 256a, respectively, which are attached, e.g., crimped or adhered, to the cord 250. By utilizing the sleeve 252a at the first end 252, the tolerance of the first end 252 relative to the opening 254 may be closely controlled without concern for the size, material, or structure of the cord 250. In one embodiment, the sleeves 252a and 256a are made of stainless steel.

The second end 256, e.g., the sleeve 256a, of the lock member 208 may be used to provide a gripping surface to assist in lock member removal. In one embodiment, the sleeve 256a may be used to secure an optional grasping loop 258 as shown in FIG. 2. The loop 258 may be sized to permit insertion of a finger to assist the clinician with lock member removal.

The lock member 208 is movable from an engaged state in which the lock member is coupled to the retainer 206 to hold the arm 210 in the second position (see, e.g., FIGS. 3 and 6), to a disengaged state in which the lock member releases the arm from the second position. The lock member 208 is preferably movable from the engaged state to the disengaged state via manipulation of the lock member from outside the skin, e.g., via application of a traction force to the second end 256 of the lock member to remove the latter from the retainer 206.

Figure 6:
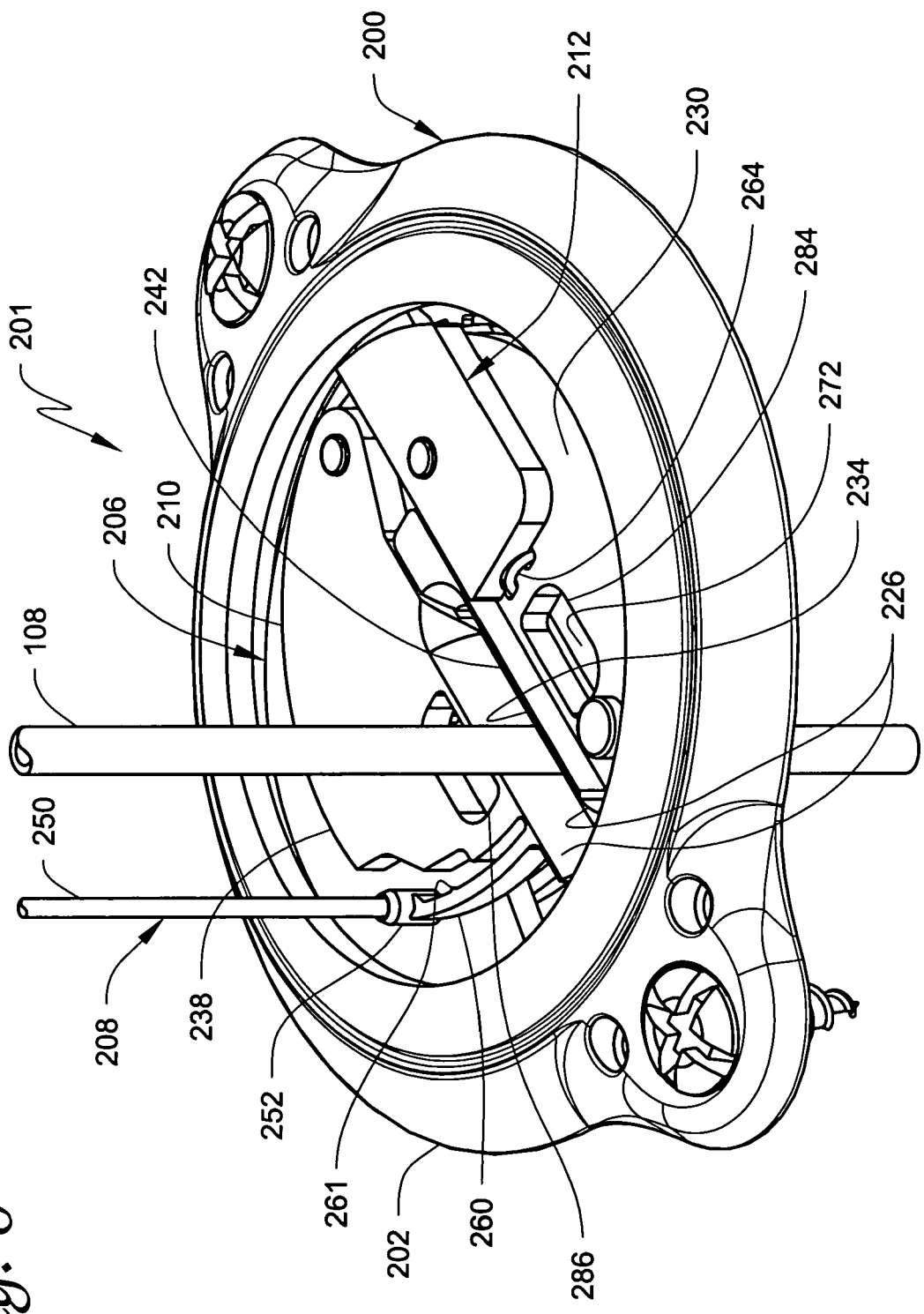
FIG. 6 is a perspective view of the anchor assembly of FIGS. 1A-1B with the retainer shown in a second or locked configuration corresponding to the arm being in a second or locked position, and the latch of the retainer shown in a second or latched position.

The lock member 208 is configured to secure or lock the arm 210, e.g., the second retaining surface 242, in the second or locked position, as shown in FIG. 6, by engaging a locking portion 260 of the arm as further described below. While not visible in FIG. 6, the arm may include a locking portion 260 on both the first plate member 238 and the second plate member 240 (see FIG. 10).

The lock member 208 may be retained within the body portion 230 via a variety of methods. For example, in one embodiment, the first end 252 may be sized such that it is received into the opening with an interference or press fit, wherein the interference provides a suitable retention force. In another embodiment, the opening 254 may form a slot that receives the first end 252. Such a slot may provide advantages including added flexibility of the body portion 230 during insertion/removal of the lock member 208. As a result, tolerance control between the first end 252 and the body portion 230 could potentially be relaxed.

In yet another embodiment, a cantilever spring may be provided that is integral or otherwise associated with the opening 254. The spring and opening may both provide a suitable retention force between the lock member 208 and the body portion 230 without necessitating the elevated tolerance accuracy typically associated for press fits. In still yet another embodiment, the first end 252 of the locking member 208 may be sized to freely slip into the opening 254. The locking portion 260 of each arm 210 could then mechanically interfere with the first end 252 to provide a frictional retention force. In one embodiment, this retention force may be about 0.1 pounds force (lbf) to about 1.1 (lbf). However, this range is exemplary only and embodiments that release upon the application of most any force are certainly possible without departing from the scope of the invention. In this embodiment, each locking portion 260 may basically form a cantilevered spring that allows insertion, despite the mechanical interference, of the first end 252 of the lock member 208 into the body portion 230. In still other embodiments, a detent bump 261 (see FIG. 6) may be provided that creates a detent action to releasably hold the arm 210 in the unlocked position. Due to the spring-like action of each locking portion 260, a suitable detent holding force may be created.

The retainer 206 may further include the latch 212 as shown in FIG. 4 (also shown in section in FIGS. 9A and 9B). The latch 212 may be used to secure the retainer 206 relative to the base 202. While shown in FIG. 4 as a separate component attached to the body portion 230, the latch 212 could, in other embodiments, be formed as an integral part of the retainer, e.g., deflectable snap fit tabs as further described below.

The latch 212 may include a latch plunger 262 that is biased outwardly by a biasing member, e.g., spring 264. The latch plunger 262 may be formed by first and second plate members 266 and 268 that are joined at a nose 270. A pin, e.g., retaining pin 271 may also extend between the plate members 266 and 268. The latch plunger 262 may thus form a clevis that extends over both sides of the body portion 230 when assembled.

The latch 212, e.g., latch plunger 262, is preferably movable from a first or unlatched position that is at or within the peripheral edge 232 of the body portion 230 (see, e.g., FIG. 5), to a second or latched position extending beyond the peripheral edge of the body portion (see, e.g., FIG. 6). The latch plunger 262 is preferably biased towards the latched position by the biasing member (e.g., by the spring 264).

A stop, such as tab 272, may be provided on one of the plate members, e.g., the lower plate member 268. The tab 272 may be used to hold the latch plunger 262 in the unlatched position. For example, the tab 272 may include an opening 274 that aligns with an opening 276 in the body portion 230 when the latch 212 (e.g., the latch plunger 262) is in the first unlatched position. A pin 278, which may be fixed (e.g., via interference or adhesive) within the opening 276, may then engage the opening 274 (preferably with clearance) to hold the latch plunger 262 in place.

The body portion 230 may further include an opening, e.g., slot 280, that receives and retains the spring 264. A finger 282 may extend into the slot 280 to assist with spring retention. The retaining pin 271, which may be installed when the latch plunger 262 is in the first or unlatched position, may also extend through the slot 280. As a result, the pin 271 may limit the outward movement of the biased latch plunger 262 and prevent component separation.

The body portion 230 may define other features, e.g., slots 284 and 285, that assist in assembly and/or manipulation of the retainer as further described below. The arm 210 may also include a slot 286 that, in conjunction with the slots 284 and 285, assists in movement of the arm.

FIG. 5 illustrates a perspective view of the anchor 200 with a portion of the base 202 cut-away to show the ledge 216 in more detail. In this view, the arm 210 is shown in the first or unlocked position and the latch 212 is shown in the first or unlatched position. As illustrated in this view, the base 202 may be of two-part construction. A first or inner portion 222 may form the ledge 216 and its associated structure (e.g., the teeth 218) to support the retainer 206. A second or outer portion 224 may include features (e.g., fastener attachment points) that assist in attaching the base 202 to tissue (bone surface) surrounding the burr hole 112. The first portion 222 may be relatively rigid (as compared to the second portion 224) to ensure that the catheter 108 is adequately immobilized. The second portion 224 is preferably more compliant than the first portion 222. The compliance of the second portion 224 allows the anchor 202 to generally conform to the local shape of the skull 113 (see FIG. 2). In one embodiment, the first or inner portion 222 of the base 202 is made from titanium, while the second or outer portion 224 is made from an implantable thermoplastic such as amorphous polyamide.

The second portion 224 may be pivotally coupled to the first portion 222 of the base 202 via a ball and socket arrangement as shown in the cut-away portion of FIG. 5. For example, the inner surface of the second portion 224 may include an inner circumferential lip 225 that is convex in cross section as shown in FIG. 5. This lip 225 may fit within an outer circumferential recess of the first portion 222 that is concave in cross section as shown in FIG. 5. While the base 202 is illustrated as having a two part construction, such a configuration is not limiting. For example, other embodiments of the base 202 may utilize a single piece construction without departing from the scope of the invention. Such a single piece construction could include integral flexing elements, or flexures, to create a rigid portion and a conforming portion of the base 202.

Other variations of the base 202 are also possible. For example, while not illustrated herein, the base 202 could be formed with a radial slot extending entirely through the ring that forms the base (e.g., yielding a C-shaped base). Such a construction may allow side loading of the base 202 over the catheter 108 after the catheter is positioned but before the stereotactic positioning apparatus is removed.

FIG. 6 illustrates the anchor 200 of the anchor assembly 201 with the latch 212 in the latched position and with the arm 210 in the locked position. In the locked position, the arm 210, e.g., the second retaining surface 242, mechanically engages the catheter 108 by clamping or pinching the catheter against the first retaining surface 234. To reduce stress on the catheter 108, curved transition surfaces 226 associated with either or both the first and second retaining surfaces 234 and 242 may be provided. As further shown in this view, the locking portion(s) 260 of the arm 210 may be configured to contact the lock member 208 (when the arm is in the locked position) such that the arm is immobilized relative to the body portion 230 of the anchor 200.

Figure 10:
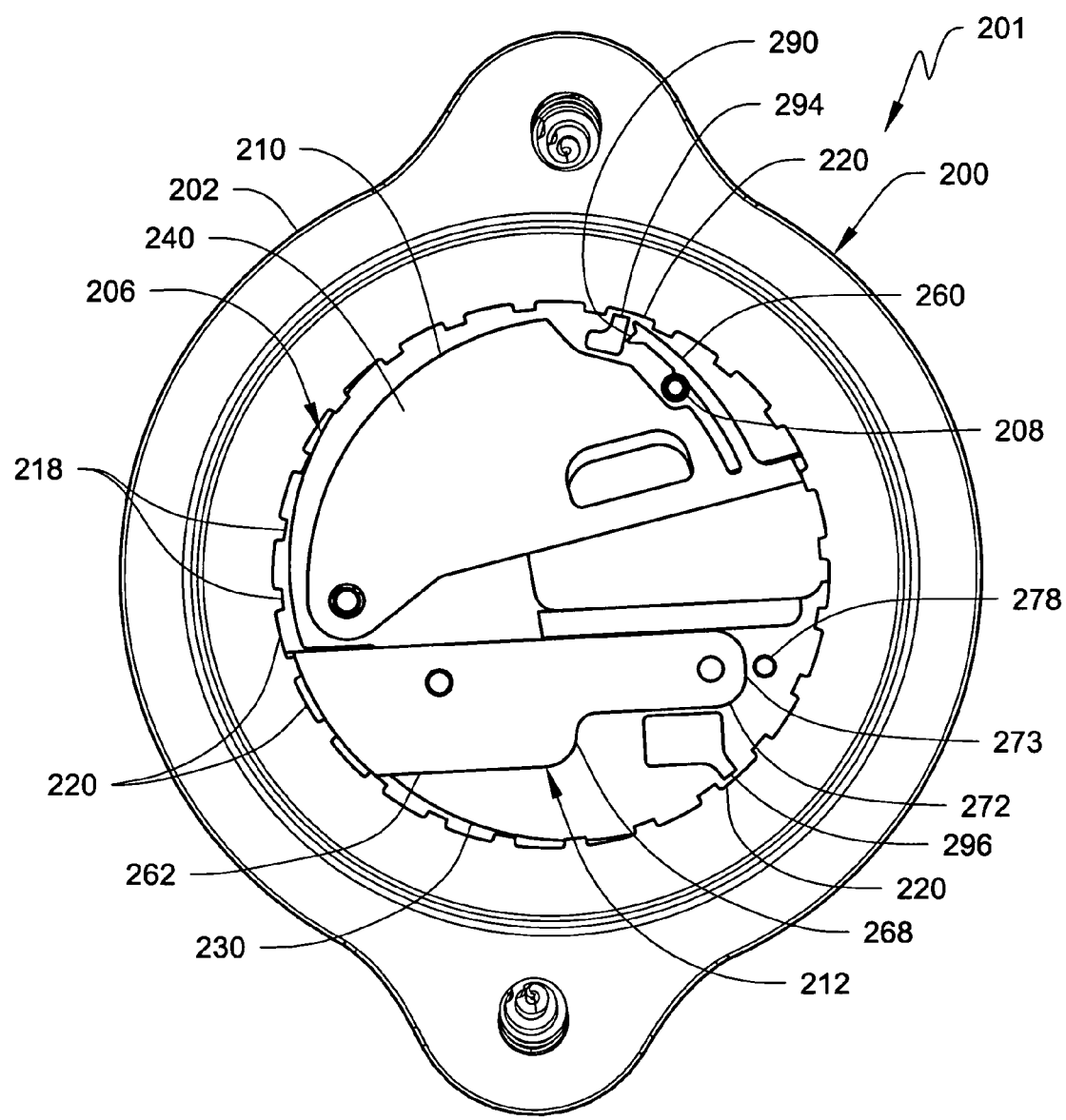
FIG. 10 is a bottom plan view of the anchor assembly of FIG. 7 with the latch shown in the latched position and the arm shown in the unlocked position.

To further illustrate the movement of the arm 210, FIGS. 7 and 8 provide, respectively, top views of the anchor assembly 201. FIG. 7 illustrates the anchor assembly with the arm in the unlocked position and the latch in the latched position, while FIG. 8 illustrated the anchor with the arm in the locked position and the latch in the latched position (the catheter 108 is removed from these views for clarity). As illustrated in FIG. 7, the locking portion 260 may form a resilient finger that may deflect to rest against the lock member 208, e.g., against the first end 252, when the arm is in the first or unlocked position. During the implantation procedure, the arm may be moved (e.g., pivoted about the pin 248) to the locked position of FIG. 8 once the catheter 108 is located at the desired position within the central opening 214. The arm 210 may be moved to the locked position by, for example, inserting an instrument such as forceps into the slots 284 and 285 and drawing the second retaining surface 242 of the arm towards the first retaining surface 234. A stop member, e.g., a protrusion 289 formed on the body portion 230, may be provided to limit the movement of the arm 210 towards the first retaining surface, thus providing protection against catheter over-compression When the arm reaches the locked position shown in FIG. 8, the locking portion(s) 260 of the arm 210 may slide past the first end 252 of the lock member 208. When the locking portion 260 clears the first end 252, it may return to an undeflected state. In this undeflected state, each locking portion 260 of the arm 210 is aligned with the first end 252 of the lock member 208 such that a lock surface 290 (see FIG. 7) abuts the first end of the lock member as shown in FIG. 8. In the illustrated embodiment, the lock surface 290 could be concave in shape to seat against the cylindrical shape of the first end 252 of the lock member 208 when the arm is in the second position. Alternatively, the lock surface 290 may be formed by one or more linear surfaces tangent to the first end 252 as best illustrated in FIGS. 7 and 10. When the lock surface 290 is engaged with the lock member 208, the arm 210, e.g., the second retaining surface 242, is held in the locked position shown in FIG. 8.

As mentioned above, the lock member 208 may be retained in the body portion 230 with an interference fit. However, in some instances, e.g., when the arm 210 is in the locked position as it is during infusion, it may be beneficial to increase the lock member retention force. Accordingly, in some embodiments, the catheter 108 may be constructed to be relatively rigid in compression as already described above. This catheter construction may increase the force applied to the first end 252 of the lock member 208 by the locking portion 260, and thus increase frictional retention of the first end within the opening 254 of the body portion 230. In one embodiment, the retention force, e.g., the force required to remove the first end 252 from the body portion 230, may be about 0.1 lbf to about 3 lbf, e.g., about 0.5 lbf to about 2 lbf.

Prior to moving the arm 210 to the locked position as described above, the retainer 206 may first be latched or secured to the base 202 using the latch 212. Preferably, the retainer 206 is secured to the base with the latch 212 before locking of the arm 210 to prevent undesirable transverse catheter movement during retainer latching.

FIG. 9A is a section view of the anchor 200 taken along line 9A-9A of FIG. 7 illustrating the latch 212 in accordance with one embodiment of the invention. However, unlike FIG. 7, FIG. 9A shows the latch in the first or unlatched position, while FIG. 9B shows generally the same view as FIG. 9A, but with the latch in the second or latched position (e.g., a true section view of FIG. 7).

As illustrated in FIG. 9A and described above, the retainer 206 may be located within the central opening 214 of the base 202 where it may positioned to rest upon the ledge 216. Once the retainer 206 is rotationally positioned, relative to the base 202, to the desired orientation, the latch 212 may be released to secure the retainer in place. In the illustrated embodiment, the latch 212 may be released by releasing the tab 272 from the pin 278. Release of the tab 272 may be accomplished by inserting a surgical instrument, e.g., forceps, through the slot 284 and applying a slight downward force to the tab as represented by arrow 287 in FIG. 9A. Alternatively, a specialized tool (not shown) may be used. This tool may provide a properly-sized actuator point, as well as an inherent limit stop, both of which may assist in the release of the tab 272. The force may deflect the tab 272, as illustrated by the broken line representation in FIG. 9A, sufficiently for the tab to release from the pin 278. Once the tab 272 is released, the spring 264 forces the latch plunger 262 away from the body 206 of the retainer 206. That is, the spring pushes the plate members 266, 268 and the nose 270 outwardly towards the base 202.

As the latch plunger 262, e.g., the nose 270, extends towards the inner portion 222 of the base 202, the spring 264 also forces the body portion 230 against the opposite side of the base as shown in FIG. 9B. When the latch 212 is fully released or engaged (as shown in FIG. 9B), the nose 270 and the body portion 230 are pressed against opposing inner surfaces of the base 202.

As illustrated in FIGS. 9A and 9B, the base 202 may define a groove 291 bounded by the ledge 216 and by an upper surface 292. The ledge and the upper surface substantially restrain the retainer 206 against movement normal to the mounting plane of the body (i.e., along an axis of the central opening). Similarly, the biasing force of the spring 264 may substantially restrain the retainer 206 against radial movement relative to the base 202. Alternatively (or in addition), a portion of the retainer (e.g., the pin 278) may form a stop that limits movement of the latch plunger 262 away from the latched position. This is accomplished, in one embodiment, by an end 273 of the tab 272. The end 273 may abut the pin 278 when movement of the latch plunger 262 away from the latched position occurs, thus assisting with maintaining the latch in the latched position. As a result, the retainer 206 may be secured within the central opening of the base 202 via the latch 212.

FIG. 10 illustrates a bottom plan view of the anchor after the latch 212 is moved to the second or latched position of FIG. 9B and before the arm is moved to the locked position. As illustrated in this view, the latch plunger 262 of the latch 212 may force the retainer 206 to a location slightly off-center from the base 202 such that the retainer and base are no longer concentric. As the retainer 206 is shifted transversely to the base, lock members, e.g., tabs 294 and 296, attached to the body portion 230 may each engage one of the recesses 220 of the base as shown. Engagement of the tabs 294, 296 with the recesses may reduce or eliminate excessive rotation of the retainer 206 relative to the base.

Embodiments of the present invention may further include methods for delivering therapy via a partially implanted device extending through a covered portal such as the skin-covered burr hole 112. For example, an exemplary method may include securing the device (e.g., catheter 108) relative to the burr hole 112 with the subdermal anchor 200. Securing the device 108 relative to the burr hole 112 may be accomplished by clamping the device between opposing retaining surfaces 234, 242 of the anchor 200 during implantation as described above. The anchor 200 may be attached to bone (e.g., to the skull) surrounding the burr hole, wherein the device 108 protrudes outwardly through the skin 111. The method may further include releasing the device 108 from the anchor 200 by manipulation of the anchor from outside the skin 111. In one embodiment, releasing the device 108 includes applying a release (e.g., traction) force to the lock member 208 protruding outwardly through the skin and removing the lock member from the anchor 200. By then applying a force (e.g., traction force) to a portion of the device 108 that protrudes outside the skin, the device may be removed entirely from the patient.

In other embodiments, methods for removing a partially implanted device (such as the catheter 108) extending through the skin-covered burr hole are provided. For example, in one embodiment, the method may include applying a release (e.g., traction) force to a lock member (e.g., lock member 208) extending through the skin 111, wherein the lock member is coupled to the subdermal anchor 200 that is used to immobilize the device relative to the burr hole 112. The lock member may be detached from the anchor 200 and withdrawn through the skin. By then applying a force (e.g., traction force) to a portion of the device 108 protruding outside the skin, the device may be removed entirely from the patient through the skin.

Figure 11A:
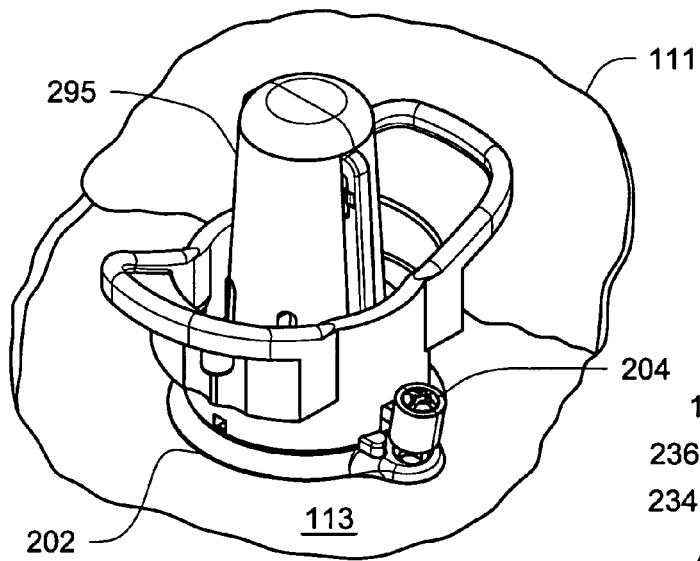

FIGS. 11A-11D illustrate an exemplary method of using the anchor assembly 201 to secure and release the catheter 108 from within the burr hole. After peeling the skin 111 back to expose the skull 113 as shown in FIG. 11A, the burr hole 112 may be formed at a predetermined location in accordance with conventional practices. The base 202 of the anchor 200 may then be attached to the skull 113. To assist with attachment of the base, an attachment tool 295 may be provided. The attachment tool may interlock with the base 202 and align the latter with the burr hole 112. Once aligned, the attachment tool 295 may also support and align the bone screws 204 that are used to secure the base 202 to the skull 113.

Once the base is attached to the skull and the tool 295 is removed, the catheter 108 may be inserted through the burr hole 112 until the tip is located at the desired location within the brain. Catheter insertion and positioning may be accomplished with stereotactic instrumentation (not shown).

Figure 11B:
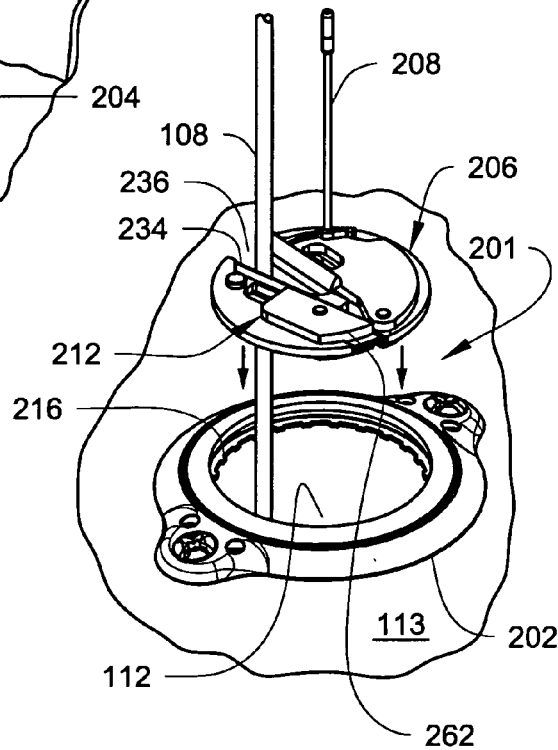

While the catheter 108 is supported with the stereotactic instrumentation, the retainer 206 (assembled as shown in FIGS. 2 and 11B with the arm in the first or unlocked position and the latch 212 in the first or unlatched position) may be side-loaded around the catheter 108 as shown in FIG. 11B such that the catheter enters the retainer via the opening 236. The retainer 206 (with the lock member 208 attached) may then be set into the base 202 where it may seat upon the ledge 216 as already described herein.

Because the catheter 108 position within the burr hole 112 may vary depending on the targeting procedure utilized, the retainer 206 is preferably operable to be rotated about its center axis. That is, the retainer 206 may be rotated within the base 202 until the first retaining surface 234, at some location along its length, approaches or contacts the catheter 108. At this point, the latch 212 may be activated to release the latch plunger 262. As described above, the latch 212 may be activated by inserting forceps or the like (not shown) into the slot 284 (see, e.g., FIG. 7) to disengage the tab 272 from the pin 278 (see, e.g., FIG. 9A). Once released, the latch 212 may secure the retainer within the base 202.

With the retainer 206 secured, the arm 210 may be moved from the first unlocked position (see, e.g., FIG. 7) to the second locked position (see, e.g., FIG. 8). As described above, movement of the arm between the first and second positions may be accomplished by grasping the openings 284 and 286 with forceps and applying a closing force.

Figure 11C:
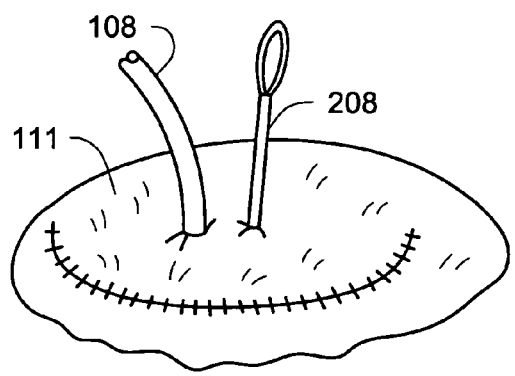

Once the catheter 108 is secured, the stereotactic instrumentation may be removed. After placing the skin flap 111 over the anchor, the incision may then be closed as shown in FIG. 11C. Two openings or punctures may be formed in the skin flap to permit the passing of the catheter 108 and the lock member 208 through the skin. For example, one possible technique may involve piercing the skin from the outside with a needle or the like (e.g., Touhy needle), after which the catheter 108 (or lock member 208) may be fed through the needle. The needle may then be withdrawn, leaving the catheter 108 (or lock member 208) extending through the skin opening. The catheter 108 may then be connected to the infusion pump 106, e.g., via the connector 120 and second tube 102 as illustrated in FIG. 1A. Infusion of the therapeutic substance in accordance with a desired therapy delivery profile may then commence.

While not illustrated, other components may be utilized to reduce bending stress on the catheter 108 during implantation. For example, an elastomer (e.g., silicone rubber) strain relief plate or disk (not shown) may be attached to the surface of the skin (e.g., with adhesive or dressing). The strain relief plate may include an opening and/or a shaped guide slot through which the catheter 108 may pass. The opening/slot preferably holds the catheter as it is draped around the scalp and may reduce bending stress on the catheter in the event that the catheter is inadvertently pulled at an angle. The plate member may also include an opening for the lock member 208 to pass. In other embodiments, the entire burr hole site may be dressed or bandaged. The bandage may include taping of the catheter to the body of the patient so as to provide the desired strain relief.

Figure 11D:
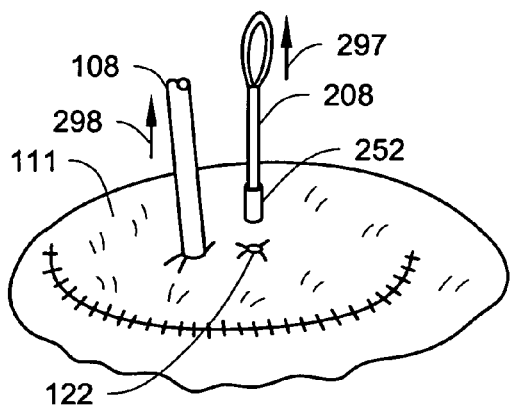

At or before the completion of therapy delivery, the lock member 208 may be removed or detached from the anchor (e.g., removed from the opening 254 in the body portion 230) and withdrawn through the skin flap 111 by, for example, application of a release (e.g., traction) force from outside the body 101 as represented by arrow 297 in FIG. 11D. Removal of the lock member 208 permits the arm 210 to release its mechanical engagement force on the catheter 108. Accordingly, the catheter may be subsequently removed from the patient by the application of a force applied to the catheter as represented by arrow 298. Depending on the size of the lock member 208 and the catheter 108, the skin punctures 122 remaining after device removal may require suturing. However, in other embodiments, the size of both components is sufficiently small such that no sutures are required.

While described above in terms of passing the catheter 108 and lock member 208 through separate openings or punctures, other embodiments are also possible. For example, the catheter 108 and/or lock member 208 may extend through the skin at the original skin flap incision. Alternatively, the catheter and lock member could be routed through a single opening or puncture. In still another embodiment, the catheter 108 could be tunneled beneath the skin to a remote location.

Figure 12A:
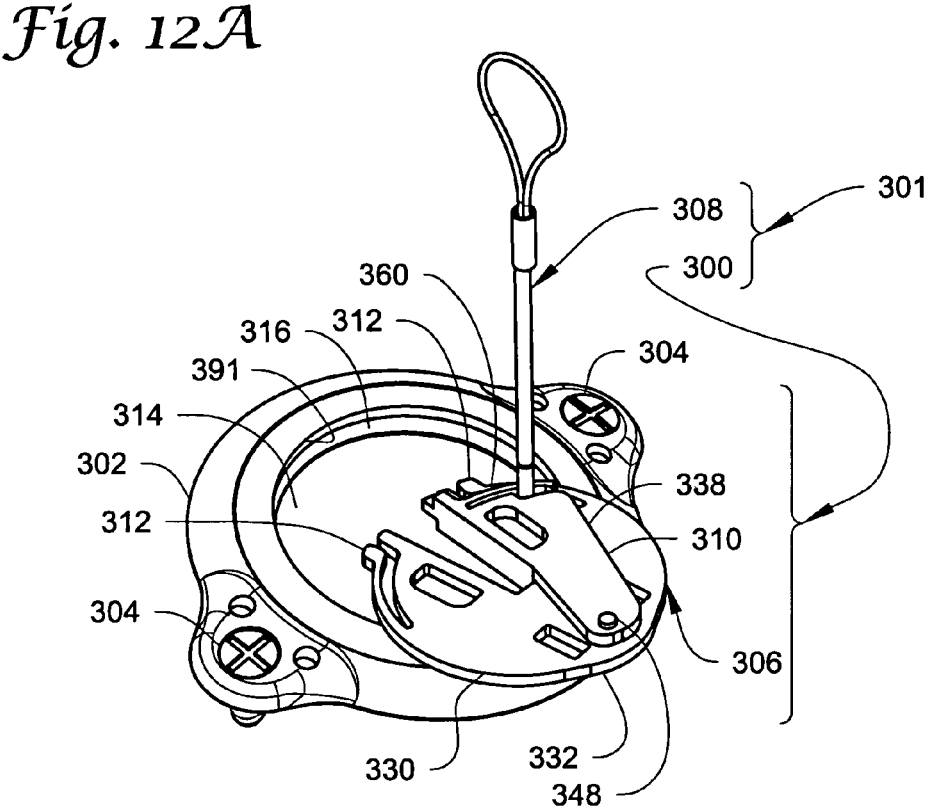
Figure 12B:
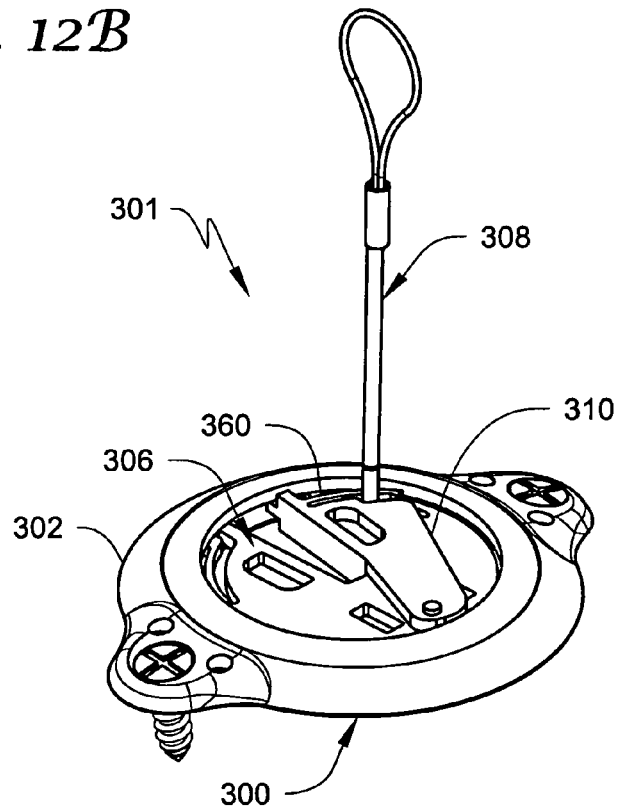

FIGS. 12A-12B illustrate an anchor assembly 301 in accordance with another embodiment of the invention. The anchor assembly 301 may include an anchor 300 that is similar to the anchor 200 described above. For example, it may include a base 302 attachable to the skull with fasteners 304, and a retainer 306 having a movable, e.g., pivoting, arm 310. The arm 310 may include first and second plate members 338, 340 (the lower plate 340 is illustrated in FIG. 14A) and locking portions 360 (see FIG. 13) that are similar in most respects to the respective components of the anchor 200 described above. The arm 310 may include an integral pin 348 formed upon an extension of the lower plate 340 that engages a corresponding opening in a body or body portion 330 of the retainer 306 to permit pivotal motion. The arm 310 is illustrated in a first or unlocked position in FIGS. 12A-12B. As with the anchor assembly 201, the anchor assembly 301 may further include a lock member 308 similar in most respects to the lock member 208 already described herein.

The base 302 may also be similar in most respects to the base 202. For example, it may define a central opening 314 to receive the retainer 306. An inner edge of base 302 may have a circumferential groove 391 formed therein. The groove 391 may be similar in many respects to the groove 291 described above. For example, it may define a ledge 316 upon which the retainer may seat. However, unlike the groove 291, the groove 391 may not require teeth (e.g., teeth 218) as the retainer 306 utilizes a latch of a different configuration.

The latch may, in the illustrated embodiment, be formed by flexible tabs 312 located on a peripheral edge 332 of the body portion 330 of the retainer 306. The tabs 312 may deflect to permit retainer insertion into the groove 391, whereafter the tabs may return to their undeflected positions. As a result, the retainer 306 may be biased against the opposite side of the base 302 as shown in FIG. 12B. Accordingly, like the latch 212, the tabs 312 are capable of biasing the retainer 306 into the groove 391 to generally secure the retainer relative to the base 302. The spring force of the tabs 312 is preferably sufficient to ensure little or no notable rotation between the retainer 306 and the base 302.

Figure 13:
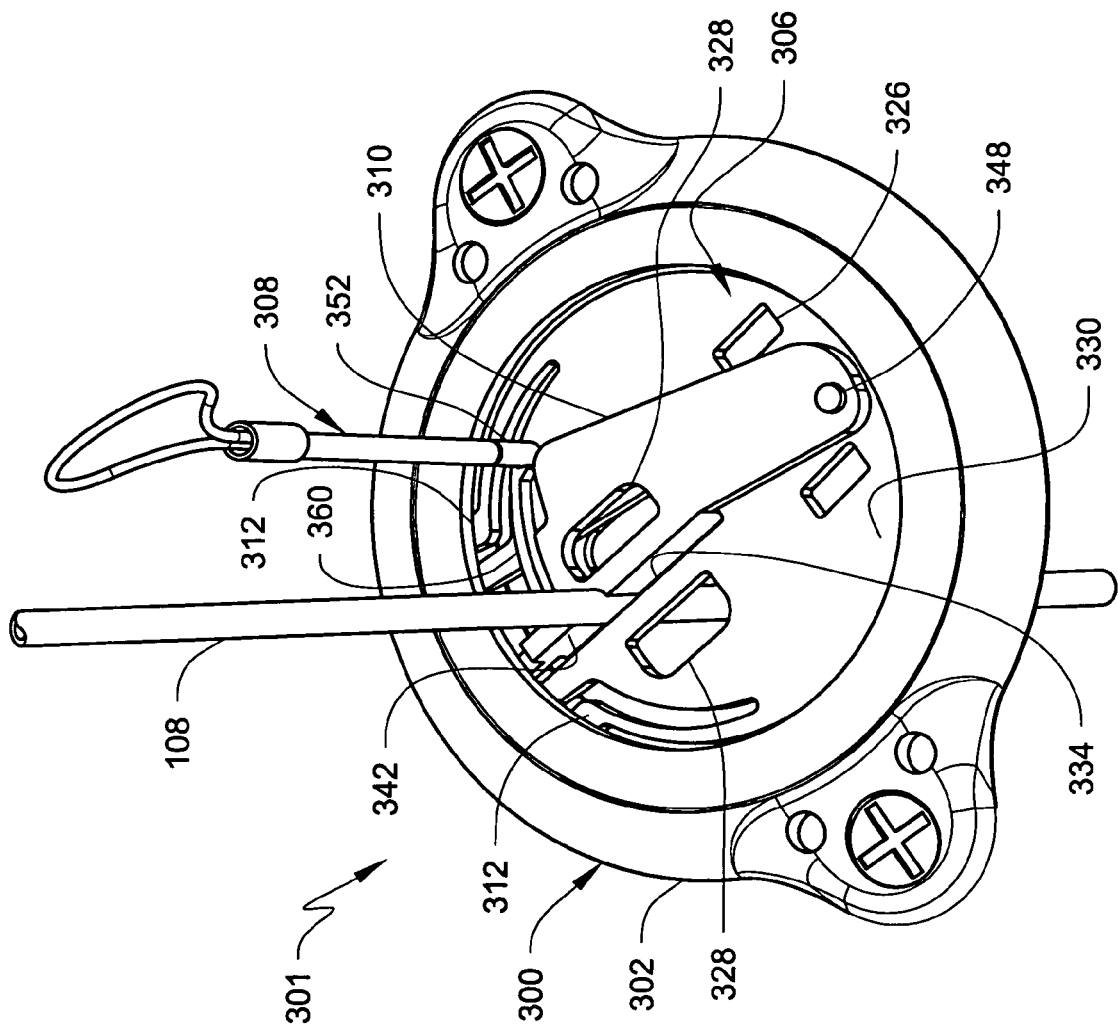
FIG. 13 is a perspective view of the anchor assembly of FIGS. 12A-12B with the retainer shown in a second or locked configuration corresponding to the arm being in a second or locked position.
Figure 14A:
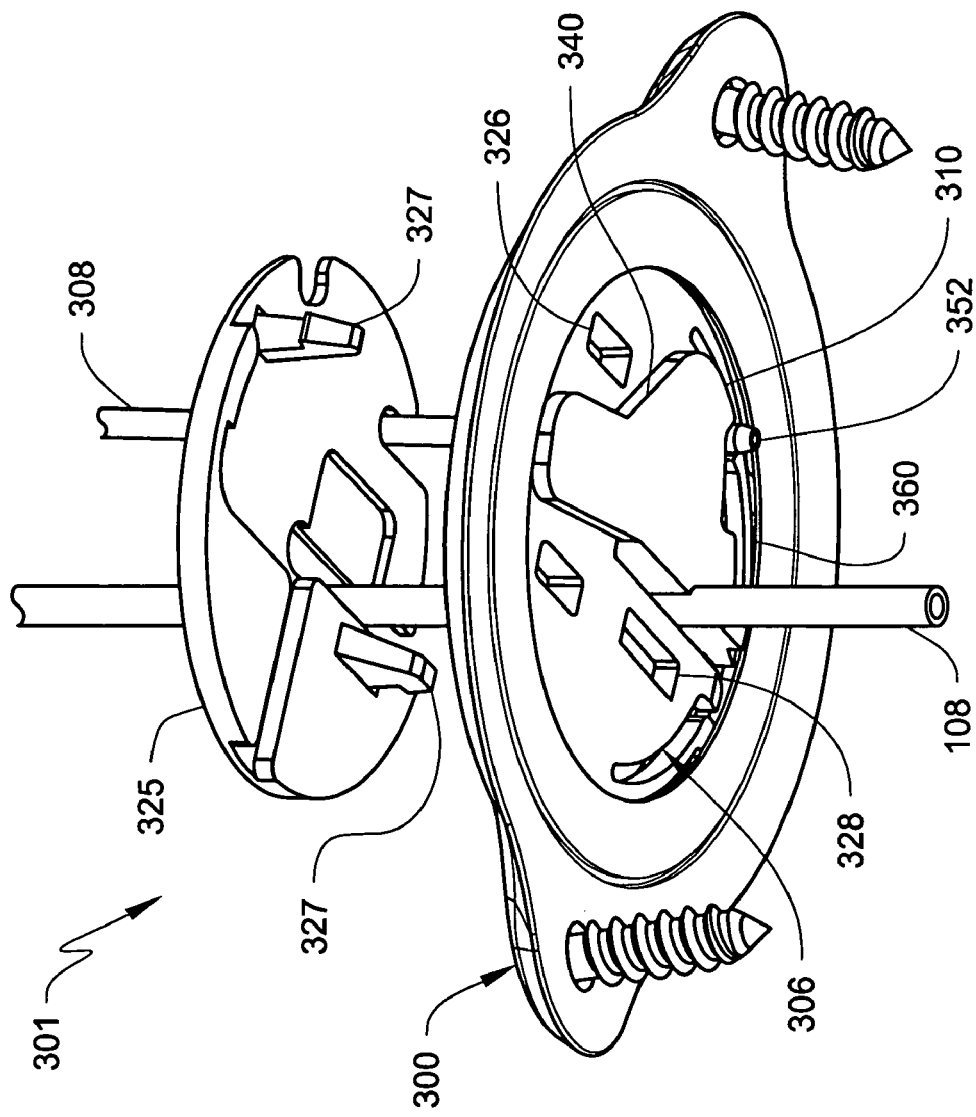

FIG. 13 is an enlarged perspective view of the anchor 300 with the arm 310 shown after pivotal movement to a second or locked position to secure the catheter 108. As with the retainer 206, the body portion 330 of the retainer 306 may form a first retaining surface 334 while the arm 310 forms a second retaining surface 342. When the arm 310 is in the first position illustrated in FIG. 12B, the second retaining surface 342 may be oblique to the first retaining surface 334 as already described above with respect to the first and second retaining surfaces 234 and 242. However, when the arm 310 is in the second position as shown in FIG. 13, the first and second retaining surfaces 334 and 342 may be generally parallel to mechanically secure the catheter 108 at most any location along a length of the slot formed by the two retaining surfaces.

As clearly shown in FIG. 13, the lock portions 360 are substantially similar to the lock portions 260 already described above. As a result, a surface of each lock portion 360 may abut the lock member 308, e.g., abut a sleeve provided at a first end 352 of the lock member, when the arm 310 is in the second position.

The retainer 306 may further include openings 326 to, for example, assist with placing the retainer within the base 302. The body portion 330 and arm 310 may also include openings or slots 328 to assist with movement of the arm to the second position via forceps or the like.

Figure 14B:
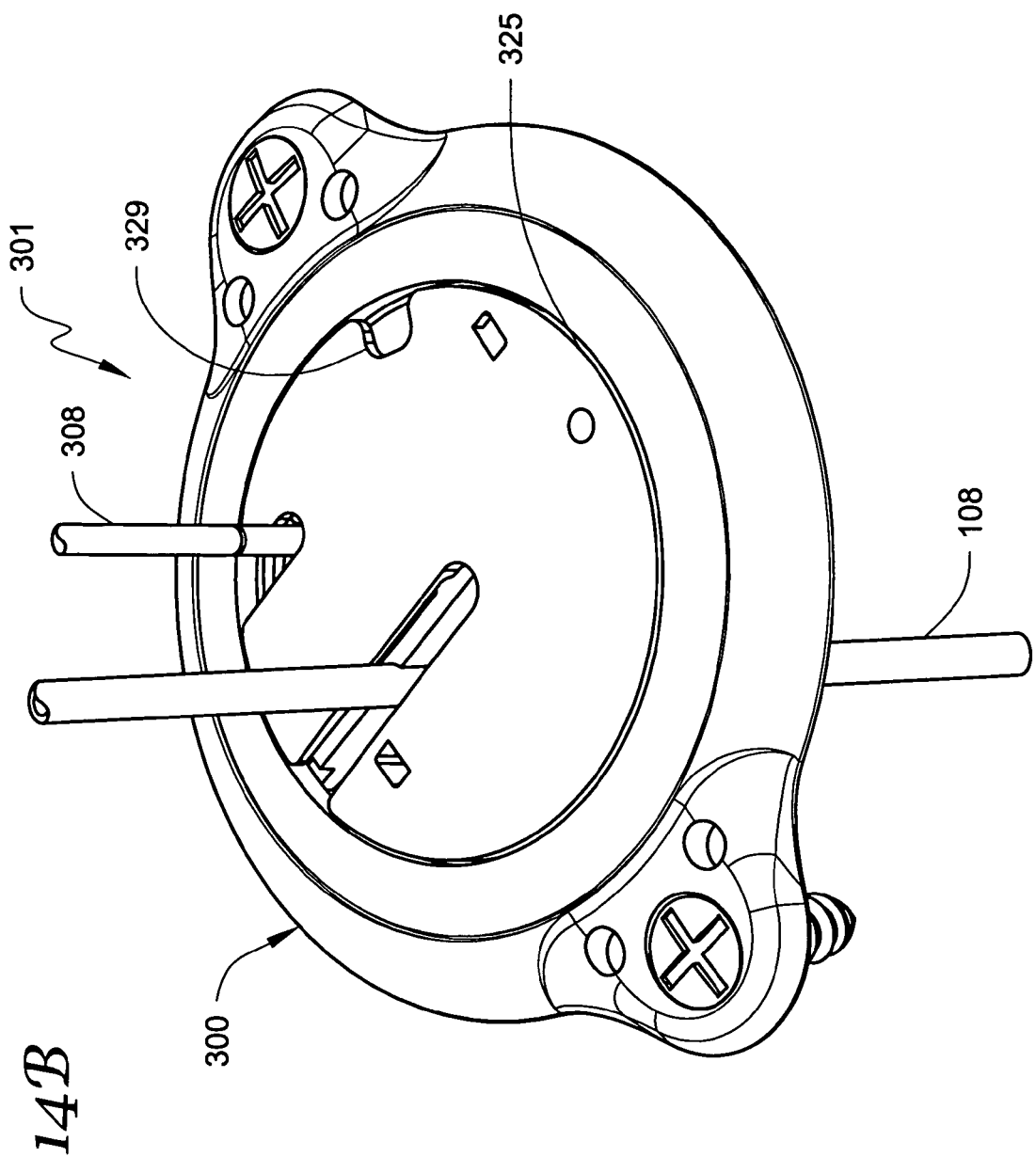

FIG. 14A is a bottom perspective view of the anchor 300 showing an optional cover 325 that may be placed over the retainer 306 after the arm 310 is moved to the second or locked position. The cover 325 may provide a smooth outer surface (as shown in FIG. 14B) to, for example, reduce stress on local tissue (e.g., skin) and limit tissue growth into the anchor 300. The cover 325 may include tabs 327 configured to securely engage one or more of the openings 326 or slots 328 in the body portion 330.

FIG. 14B illustrates a top perspective view of the anchor 300 with the cover 325 installed. As shown, the cover may include a slot to permit side loading of the cover over the catheter 108 after catheter immobilization. A corresponding slot may be provided to accommodate the lock member 308. To assist with removal of the cover 325, a cutout 329 may be provided.

FIGS. 15A-15D illustrate an anchor assembly 401 in accordance with still yet another embodiment of the invention. The anchor assembly 401 is similar to the anchor assemblies 201 and 301 described above. For example, it includes an anchor 400 having a base 402 attachable to the skull with fasteners 404, and a retainer 406 having a body or body portion 430 and a movable, e.g., pivoting, arm 410. Like the arm 310, the arm 410 may include an integral pin 448 that engages a corresponding opening in a body portion 430 of the retainer 406. The arm may include a first plate member 438 and a second plate member 440 (see FIG. 15D) that are similar in most respects to the respective components of the anchor 300 described above. The arm 410 is illustrated in a first or unlocked position in FIG. 15A. The anchor assembly 401 may also include a lock member 408 similar to the lock members 208 and 308 already described herein.

The base 402 may also be similar in most respects to the bases 202 and 302. For example, it may define a central opening 414 to receive the retainer 406. An inner edge of the base 402 may further have a circumferential groove 491 formed therein. The groove 491 may be similar in many respects to the groove 391 described above. For example, it may define a ledge 416 upon which the retainer 406 may seat.

The retainer 406 may include a latch formed by flexible tabs 412 on a peripheral edge of the body 430 of the retainer. The tabs 412 are substantially identical to the tabs 312 already described above. Accordingly, like the latch 212, the tabs 412 are capable of biasing the retainer 406 into the groove 491 to generally secure the retainer to the base.

While the retainer 406 may be secured to the base 402 in a manner substantially identical to the retainer 306 and base 302 already described herein, movement of the arm 410 from the first position (FIG. 15A) to a second or locked position (FIG. 15B) may be achieved as described below.

The retainer 406 may incorporate a lock portion configured as a tab member 451 slidable within a slot 453 formed in the body 430 of the retainer. When the tab member 451 and the lock member 408 are retracted within the slot 453 as shown in FIG. 15A, the arm 410 is moved to the first or unlocked position. However, once the catheter 108 is located between first and second retaining surfaces 434 and 442, the arm 410 may be moved from the first position (in which the second retaining surface is oblique to the first retaining surface as already described above with respect to the surfaces 234 and 242) to the second or locked position illustrated in FIG. 15B. In the second position, the first and second retaining surfaces 434 and 442 are generally parallel to one another to secure the catheter 108 at most any location along the slot formed by the retaining surfaces.

Figure 15D:
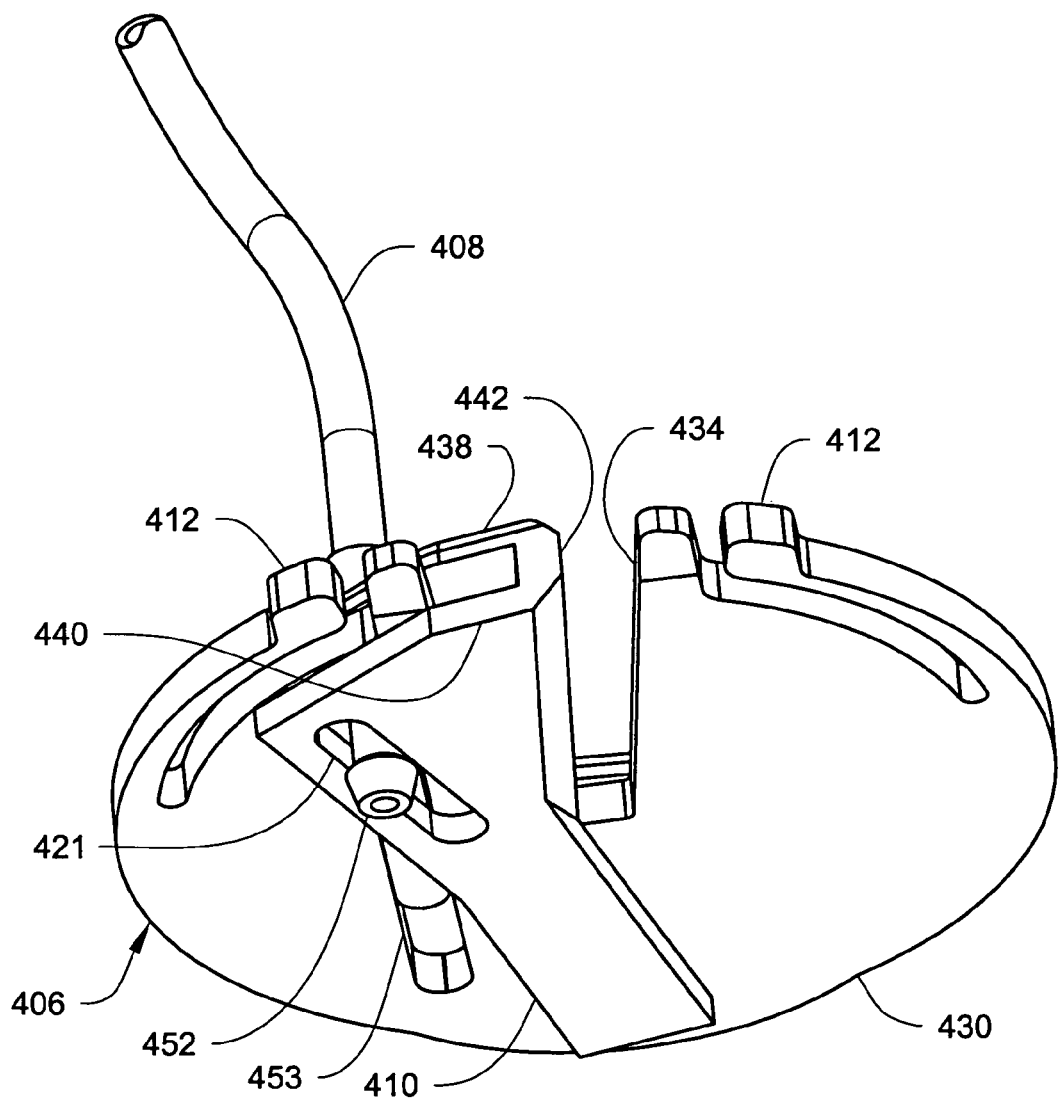

To move the arm 410 to the second or locked position, the tab member 451 may be slid within the slot 453 in the direction indicated in FIG. 15B. As the tab member 451 slides along the slot 453, it forces a first end 452 of the lock member 408 into contact with a ramped edge 455 of the arm 410, causing the arm, e.g., the second retaining surface 442, to move towards the first retaining surface 434. The underside of the arm 410 may further include a slot 421 to accommodate movement of the lock member as shown in FIG. 15D. When the tab member 451 reaches a location along the slot 453 corresponding to the arm 410, e.g., second retaining surface 442, being in the desired locked position as shown in FIG. 15B, the tab member may engage a detent (not shown) formed in the body 430. As a result, the arm 410 may be secured in the second position of FIG. 15B.

The lock member 408 may be withdrawn, e.g., at therapy completion, from the anchor in a manner similar to that described above with respect to the anchor 200 and lock member 208. With the lock member 408 removed from the anchor 400, the arm 410 is free to pivot back towards the first unlocked position as indicated in FIG. 15C by arrow 417, thereby releasing the retention force on the catheter 108. As a result, the catheter may be withdrawn from the burr hole via the application of a traction force represented by arrow 419.

FIG. 15D is a bottom perspective view of the anchor 400 illustrating an exemplary configuration of the arm 410. As illustrated in this view, the second plate member 440 may include an extension that forms the integral pin 448 about which the arm 410 pivots. The second plate member 440 may further define the slot 421 operable to receive the first end 452 of the lock member 408. The slot 421 may transform the linear movement of the tab member 451 into pivotal movement of the arm 410. The components of the assembly 401, as well as of the assembly 301, may be constructed of materials similar to those discussed elsewhere herein with respect to the corresponding components of the assembly 201.

Anchors and anchor assemblies in accordance with embodiments of the present invention may permit anchoring of a device (such as a medical catheter or an electrical lead) relative to a surface portal. While such anchor assemblies may be advantageous in many applications, they may be particularly useful in medical applications wherein the anchor is subdermally located as may be the case with burr hole access procedures.

Moreover, embodiments of the present invention provide anchor assemblies and methods that permit removal of the device at therapy completion without necessitating a separate surgical procedure. For example, the anchor assembly may include a lock member that protrudes outside of the skin such that it is capable of manipulation from outside the patient's body. As a result, the lock member may be manipulated and/or removed by the clinician to release the implanted device at therapy completion without surgery. This configuration is not limiting, however, as alternative anchor assemblies may use other mechanical and non-mechanical lock configurations. For example, the anchor assembly may utilize a magnetic latch that may be manipulated by a magnet positionable outside the skin but in close proximity to the anchor. Similarly, a lock that may be released by a remote radio or ultrasonic energy transmitter could be used.

The complete disclosure of the patents, patent documents, and publications cited in the Background, the Detailed Description of Exemplary Embodiments, and elsewhere herein are incorporated by reference in their entirety as if each were individually incorporated.

Illustrative embodiments of this invention are described and reference has been made to possible variations within the scope of this invention. These and other variations, combinations, and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. An anchor assembly for securing a device relative to a skin-covered portal, the anchor assembly comprising:
   a retainer positionable in or near the portal and beneath the skin, the retainer comprising:
      a body portion including a peripheral edge and a first retaining surface; and
      an arm attached to the body portion, the arm comprising a second retaining surface movable, relative to the first retaining surface, between a first position and a second position; and
   a lock member comprising an elongate cord removably coupled to the body portion, the lock member movable from an engaged state in which the lock member holds the arm in the second position, to a disengaged state in which the lock member releases the arm from the second position, wherein the lock member is movable from the engaged state to the disengaged state via manipulation of the lock member from outside the skin.

2. The anchor assembly of claim 1, further comprising a base attachable to tissue surrounding the portal, the base to support the peripheral edge of the body portion.

3. The anchor assembly of claim 1, wherein the arm is pivotally coupled to the body portion.

4. The anchor assembly of claim 1, wherein the elongate cord protrudes generally orthogonally from a plane of the body portion.

5. The anchor assembly of claim 1, wherein the retainer further comprises a latch comprising a latch plunger movable from a first position at or within the peripheral edge of the body portion, to a second position extending beyond the peripheral edge of the body portion.

6. The anchor assembly of claim 5, wherein the latch comprises a biasing member capable of moving the latch plunger.

7. The anchor assembly of claim 6, wherein the biasing member comprises a spring.

8. An anchor assembly for securing a therapy delivery device relative to a burr hole, the anchor assembly comprising:
   an anchor comprising:
      a base comprising a peripheral portion defining a central opening; and
      a retainer attachable to the base in or near the central opening, the retainer comprising:
         a body portion defining a mounting plane, the body portion comprising a peripheral edge and a first retaining surface formed by an edge of an opening extending through the peripheral edge; and
         an arm movably attached to the body portion, the arm comprising a second retaining surface movable, relative to the first retaining surface, between a first position and a second position; and
   a lock member comprising an elongate cord detachably received within an opening formed in the body portion of the retainer such that the lock member protrudes outwardly in a direction generally orthogonally from the mounting plane of the body portion.

9. The anchor assembly of claim 8, wherein the anchor is operable to be located beneath skin covering the burr hole, and the lock member is configured to extend outwardly through the skin.

10. The anchor assembly of claim 8, wherein the base further comprises a ledge formed along an inner surface of the peripheral portion, the ledge to receive and support the peripheral edge of the body portion.

11. The anchor assembly of claim 10, wherein the inner surface comprises a plurality of teeth protruding into the central opening, and wherein a recess is defined between adjacent pairs of the plurality of teeth.

12. The anchor assembly of claim 11, wherein the body portion further comprises a tab to engage the recess.

13. The anchor assembly of claim 8, wherein the retainer further comprises a latch comprising a latch plunger biased towards a latched position beyond the peripheral edge of the body portion.

14. The anchor assembly of claim 13, wherein the latch further comprises a stop to hold the latch plunger in an unlatched position within the peripheral edge of the body portion.

15. The anchor assembly of claim 13, wherein the latch further comprises a spring to bias the latch plunger towards the latched position.

16. The anchor assembly of claim 13, wherein a portion of the retainer forms a stop that limits movement of the latch plunger away from the latched position.

17. The anchor assembly of claim 8, wherein the arm is pivotally coupled to the body portion.

18. The anchor assembly of claim 8, wherein the arm comprises a lock surface that abuts the cord when the and is in the second position.

19. The anchor assembly of claim 8, wherein the peripheral portion of the base comprises: an inner portion to support the retainer; and an outer portion to secure the base to a bone surface surrounding the burr hole.

20. The anchor assembly of claim 19, wherein the outer portion is pivotally coupled to the inner portion.

21. An anchor assembly for securing a therapy delivery device relative to a burr hole, the anchor assembly comprising:
   an anchor comprising:
      a base including a peripheral portion defining a central opening, the peripheral portion comprising a ledge formed by a plurality of teeth extending into the central opening;
      a retainer positionable on the ledge, the retainer comprising:
         a body portion defining a mounting plane, the body portion having a peripheral edge and a first retaining surface formed by an edge of an opening extending through the peripheral edge, the first retaining surface spanning from an interior of the body portion to a location at or near the peripheral edge;
         an arm pivotally attached to the body portion, the arm comprising a second retaining surface movable, relative to the first retaining surface, between a first position in which the second retaining surface is oblique to the first retaining surface, and a second position in which the first and second retaining surfaces are generally parallel; and
         a latch comprising a latch plunger biased towards a latched position beyond the peripheral edge of the body portion; and
   a lock member comprising a first end insertable into a lock opening in the body portion such that the lock member protrudes away from the body portion and outwardly in a direction generally orthogonal to the mounting plane.

22. The anchor assembly of claim 21, wherein the latch further comprises a stop to hold the latch plunger in an unlatched position within the peripheral edge of the body portion.

23. A method for removing a partially implanted device extending through a skin-covered burr hole, the method comprising:
   securing the device relative to the burr hole with an anchor assembly, the anchor assembly comprising a subdermal anchor fixed relative to bone surrounding the burr hole, wherein the device protrudes outwardly through skin;
   releasing the device from the anchor by manipulation of the anchor assembly while the anchor is covered by the skin, wherein releasing the device comprises applying a release force to a release cord attached to the anchor, the release cord protruding outwardly through the skin; and
   applying a force to a portion of the device that protrudes outside the skin to remove the device.

24. The method of claim 23, wherein securing the device relative to the burr hole comprises securing the device between opposing retaining surfaces of the anchor.

25. A method for removing a partially implanted device extending through a skin-covered burr hole, the method comprising:
   securing the device relative to the burr hole with an anchor assembly, the anchor assembly comprising a subdermal anchor fixed relative to bone surrounding the burr hole, wherein the device protrudes outwardly through skin;
   releasing the device from the anchor by manipulation of the anchor assembly from outside the skin, wherein releasing the device comprises applying a release force to a release cord attached to the anchor, the release cord protruding outwardly through the skin; and
   applying a force to a portion of the device that protrudes outside the skin to remove the device.

* * * * *